(12) United States Patent
Sgroi, Jr.

(10) Patent No.: US 11,344,309 B2
(45) Date of Patent: May 31, 2022

(54) CIRCULAR STAPLING INSTRUMENTS

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 276 days.

(21) Appl. No.: 16/503,857

(22) Filed: Jul. 5, 2019

(65) Prior Publication Data

US 2021/0000473 A1 Jan. 7, 2021

(51) Int. Cl.
| | | |
|---|---|---|
| *A61B 17/34* | (2006.01) | |
| *A61B 17/115* | (2006.01) | |
| *A61B 17/068* | (2006.01) | |
| *A61B 17/10* | (2006.01) | |
| *A61B 17/3205* | (2006.01) | |
| *A61B 17/072* | (2006.01) | |

(52) U.S. Cl.
CPC ........ *A61B 17/1155* (2013.01); *A61B 17/068* (2013.01); *A61B 17/10* (2013.01); *A61B 17/32053* (2013.01); *A61B 17/34* (2013.01); *A61B 2017/07257* (2013.01); *A61B 2017/07285* (2013.01)

(58) Field of Classification Search
CPC ... A61B 17/1155; A61B 17/068; A61B 17/10; A61B 17/32053; A61B 17/34; A61B 2017/07257; A61B 2017/07285; A61B 2017/0046; A61B 2017/00473; A61B 2017/00477
USPC ...................... 227/175.1–182.1; 606/75, 219
See application file for complete search history.

(56) References Cited

U.S. PATENT DOCUMENTS

| | | |
|---|---|---|
| 3,079,608 A | 3/1963 | Babkin |
| 3,080,564 A | 3/1963 | Strekopov et al. |
| 3,193,165 A | 7/1965 | Akhalaya et al. |
| 3,252,643 A | 5/1966 | Strekopov et al. |
| 3,388,847 A | 6/1968 | Kasulin et al. |
| 3,552,626 A | 1/1971 | Astafiev et al. |
| 3,593,903 A | 7/1971 | Astafiev et al. |
| 3,692,224 A | 9/1972 | Astafiev et al. |

(Continued)

FOREIGN PATENT DOCUMENTS

| | | |
|---|---|---|
| CA | 908529 A | 8/1972 |
| CA | 1136020 A1 | 11/1982 |

(Continued)

OTHER PUBLICATIONS

European Search Report dated Feb. 25, 2021, issued in correspondingn European Application No. 20183900, 11 pages.

(Continued)

*Primary Examiner* — Robert F Long

(57) ABSTRACT

A surgical system includes an adapter assembly and a tip protector. The adapter assembly includes a tubular housing, and a trocar assembly selectively receivable in the tubular housing. The tip protector includes a housing defining a channel therethrough configured for receipt of the trocar member, a first locking member movably coupled to the housing and configured to selectively engage the trocar member to lock the tip protector to the trocar member, and a second locking member movably coupled to the housing and configured to selectively engage a distal end portion of the tubular housing to lock the tip protector to the tubular housing.

16 Claims, 12 Drawing Sheets

(56) References Cited

U.S. PATENT DOCUMENTS

| | | | |
|---|---|---|---|
| 3,795,034 | A | 3/1974 | Strekopytov et al. |
| 3,822,818 | A | 7/1974 | Strekopytov et al. |
| 4,111,206 | A | 9/1978 | Vishnevsky et al. |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,305,539 | A | 12/1981 | Korolkov et al. |
| 4,319,576 | A | 3/1982 | Rothfuss |
| 4,351,466 | A | 9/1982 | Noiles |
| 4,379,457 | A | 4/1983 | Gravener et al. |
| 4,442,964 | A | 4/1984 | Becht |
| 4,473,077 | A | 9/1984 | Noiles et al. |
| 4,476,863 | A | 10/1984 | Kanshin et al. |
| 4,485,817 | A | 12/1984 | Swiggett |
| 4,488,523 | A | 12/1984 | Shichman |
| 4,505,272 | A | 3/1985 | Utyamyshev et al. |
| 4,505,414 | A | 3/1985 | Filipi |
| 4,513,746 | A | 4/1985 | Aranyi et al. |
| 4,527,724 | A | 7/1985 | Chow et al. |
| 4,573,468 | A | 3/1986 | Conta et al. |
| 4,576,167 | A | 3/1986 | Noiles |
| 4,585,153 | A | 4/1986 | Failla et al. |
| 4,589,413 | A | 5/1986 | Malyshev et al. |
| 4,591,085 | A | 5/1986 | Di Giovanni |
| 4,592,354 | A | 6/1986 | Rothfuss |
| 4,603,693 | A | 8/1986 | Conta et al. |
| 4,605,004 | A | 8/1986 | Di Giovanni et al. |
| 4,606,343 | A | 8/1986 | Conta et al. |
| 4,606,344 | A | 8/1986 | Di Giovanni |
| 4,606,345 | A | 8/1986 | Dorband et al. |
| 4,607,636 | A | 8/1986 | Kula et al. |
| 4,615,474 | A | 10/1986 | Strekopytov et al. |
| 4,617,928 | A | 10/1986 | Alfranca |
| 4,646,745 | A | 3/1987 | Noiles |
| 4,671,445 | A | 6/1987 | Barker et al. |
| 4,681,108 | A | 7/1987 | Rosati et al. |
| 4,700,703 | A | 10/1987 | Resnick et al. |
| 4,708,141 | A | 11/1987 | Inoue et al. |
| 4,741,336 | A | 5/1988 | Failla et al. |
| 4,752,024 | A | 6/1988 | Green et al. |
| 4,754,909 | A | 7/1988 | Barker et al. |
| 4,817,847 | A | 4/1989 | Redtenbacher et al. |
| 4,848,637 | A | 7/1989 | Pruitt |
| 4,893,622 | A | 1/1990 | Green et al. |
| 4,903,697 | A | 2/1990 | Resnick et al. |
| 4,907,591 | A | 3/1990 | Vasconcellos et al. |
| 4,917,114 | A | 4/1990 | Green et al. |
| 4,930,503 | A | 6/1990 | Pruitt |
| 4,938,408 | A | 7/1990 | Bedi et al. |
| 4,941,623 | A | 7/1990 | Pruitt |
| 4,957,499 | A | 9/1990 | Lipatov et al. |
| 4,964,559 | A | 10/1990 | Deniega et al. |
| 5,005,749 | A | 4/1991 | Aranyi |
| 5,018,657 | A | 5/1991 | Pedlick et al. |
| 5,027,834 | A | 7/1991 | Pruitt |
| 5,040,715 | A | 8/1991 | Green et al. |
| 5,071,430 | A * | 12/1991 | de Salis ........... A61B 17/07207 606/219 |
| 5,104,025 | A | 4/1992 | Main et al. |
| 5,122,156 | A | 6/1992 | Granger et al. |
| 5,137,198 | A | 8/1992 | Nobis et al. |
| 5,139,513 | A | 8/1992 | Segato |
| 5,197,648 | A | 3/1993 | Gingold |
| 5,197,649 | A | 3/1993 | Bessler et al. |
| 5,205,459 | A | 4/1993 | Brinkerhoff et al. |
| 5,222,963 | A | 6/1993 | Brinkerhoff et al. |
| 5,261,920 | A | 11/1993 | Main et al. |
| 5,271,543 | A | 12/1993 | Grant et al. |
| 5,271,544 | A | 12/1993 | Fox et al. |
| 5,292,053 | A | 3/1994 | Bilotti et al. |
| 5,309,927 | A | 5/1994 | Welch |
| 5,312,024 | A | 5/1994 | Grant et al. |
| 5,333,773 | A | 8/1994 | Main et al. |
| 5,350,104 | A * | 9/1994 | Main .................... A61B 17/115 227/179.1 |
| 5,404,870 | A * | 4/1995 | Brinkerhoff ........... A61B 17/00 227/175.1 |
| 5,443,198 | A | 8/1995 | Viola et al. |
| 5,474,223 | A | 12/1995 | Viola et al. |
| 5,915,616 | A | 6/1999 | Viola et al. |
| 7,407,075 | B2 | 8/2008 | Holsten et al. |
| 7,481,349 | B2 | 1/2009 | Holsten et al. |
| 7,708,182 | B2 | 5/2010 | Viola |
| 7,722,610 | B2 | 5/2010 | Viola et al. |
| 7,793,813 | B2 | 9/2010 | Bettuchi |
| 7,803,151 | B2 | 9/2010 | Whitman |
| 7,828,188 | B2 | 11/2010 | Jankowski |
| 7,837,081 | B2 | 11/2010 | Holsten et al. |
| 7,866,527 | B2 | 1/2011 | Hall et al. |
| 8,028,884 | B2 | 10/2011 | Sniffin et al. |
| 8,070,035 | B2 | 12/2011 | Holsten et al. |
| 8,091,756 | B2 | 1/2012 | Viola |
| 8,100,310 | B2 | 1/2012 | Zemlok |
| 8,113,406 | B2 | 2/2012 | Holsten et al. |
| 8,113,407 | B2 | 2/2012 | Holsten et al. |
| 8,113,410 | B2 | 2/2012 | Hall et al. |
| 8,123,100 | B2 | 2/2012 | Holsten et al. |
| 8,123,103 | B2 | 2/2012 | Milliman |
| 8,142,475 | B2 | 3/2012 | Viola |
| 8,146,791 | B2 | 4/2012 | Bettuchi et al. |
| 8,161,977 | B2 | 4/2012 | Shelton, IV et al. |
| 8,186,556 | B2 | 5/2012 | Viola |
| 8,210,414 | B2 | 7/2012 | Bettuchi et al. |
| 8,211,130 | B2 | 7/2012 | Viola |
| 8,225,799 | B2 | 7/2012 | Bettuchi |
| 8,231,040 | B2 | 7/2012 | Zemlok et al. |
| 8,236,015 | B2 | 8/2012 | Bettuchi et al. |
| 8,256,655 | B2 | 9/2012 | Sniffin et al. |
| 8,292,147 | B2 | 10/2012 | Viola |
| 8,292,153 | B2 | 10/2012 | Jankowski |
| 8,292,155 | B2 | 10/2012 | Shelton, IV et al. |
| 8,312,885 | B2 | 11/2012 | Bettuchi et al. |
| 8,317,070 | B2 | 11/2012 | Hueil et al. |
| 8,322,455 | B2 | 12/2012 | Shelton, IV et al. |
| 8,322,588 | B2 | 12/2012 | Viola |
| 8,342,380 | B2 | 1/2013 | Viola |
| 8,361,092 | B1 | 1/2013 | Asfora |
| 8,381,961 | B2 | 2/2013 | Holsten et al. |
| 8,397,971 | B2 | 3/2013 | Yates et al. |
| 8,453,907 | B2 | 6/2013 | Laurent et al. |
| 8,453,910 | B2 | 6/2013 | Bettuchi et al. |
| 8,459,524 | B2 | 6/2013 | Pribanic et al. |
| 8,464,923 | B2 | 6/2013 | Shelton, IV |
| 8,479,968 | B2 | 7/2013 | Hodgkinson et al. |
| 8,490,853 | B2 | 7/2013 | Criscuolo et al. |
| 8,529,819 | B2 | 9/2013 | Ostapoff et al. |
| 8,544,712 | B2 | 10/2013 | Jankowski |
| 8,573,465 | B2 | 11/2013 | Shelton, IV |
| 8,602,287 | B2 | 12/2013 | Yates et al. |
| 8,602,288 | B2 | 12/2013 | Shelton, IV et al. |
| 8,608,045 | B2 | 12/2013 | Smith et al. |
| 8,622,275 | B2 | 1/2014 | Baxter, III et al. |
| 8,631,988 | B2 | 1/2014 | Viola |
| 8,636,187 | B2 | 1/2014 | Hueil et al. |
| 8,636,736 | B2 | 1/2014 | Yates et al. |
| 8,652,120 | B2 | 2/2014 | Giordano et al. |
| 8,662,371 | B2 | 3/2014 | Viola |
| 8,701,962 | B2 | 4/2014 | Kostrzewski |
| 8,746,530 | B2 | 6/2014 | Giordano et al. |
| 8,763,879 | B2 | 7/2014 | Shelton, IV et al. |
| 8,789,737 | B2 | 7/2014 | Hodgkinson et al. |
| 8,800,838 | B2 | 8/2014 | Shelton, IV |
| 8,801,735 | B2 | 8/2014 | Shelton, IV et al. |
| 8,808,311 | B2 | 8/2014 | Heinrich et al. |
| 8,820,603 | B2 | 9/2014 | Shelton, IV et al. |
| 8,840,004 | B2 | 9/2014 | Holsten et al. |
| 8,870,050 | B2 | 10/2014 | Hodgkinson |
| 8,875,970 | B2 | 11/2014 | Viola |
| 8,899,465 | B2 | 12/2014 | Shelton, IV et al. |
| 8,925,788 | B2 | 1/2015 | Hess et al. |
| 8,931,682 | B2 | 1/2015 | Timm et al. |
| 8,950,646 | B2 | 2/2015 | Viola |

(56) References Cited

U.S. PATENT DOCUMENTS

| | | |
|---|---|---|
| 8,967,445 B2 | 3/2015 | Kostrzewski |
| 8,973,804 B2 | 3/2015 | Hess et al. |
| 8,978,954 B2 * | 3/2015 | Shelton, IV ..... A61B 17/07207 227/175.1 |
| 8,991,677 B2 | 3/2015 | Moore et al. |
| 8,998,058 B2 | 4/2015 | Moore et al. |
| 9,005,230 B2 | 4/2015 | Yates et al. |
| 9,005,243 B2 | 4/2015 | Stopek et al. |
| 9,010,609 B2 | 4/2015 | Carter et al. |
| 9,028,528 B2 | 5/2015 | Bettuchi et al. |
| 9,044,230 B2 | 6/2015 | Morgan et al. |
| 9,072,535 B2 | 7/2015 | Shelton, IV et al. |
| 9,084,601 B2 | 7/2015 | Moore et al. |
| 9,084,602 B2 | 7/2015 | Gleiman |
| 9,095,339 B2 | 8/2015 | Moore et al. |
| 9,107,665 B2 | 8/2015 | Hodgkinson et al. |
| 9,107,667 B2 | 8/2015 | Hodgkinson |
| 9,113,870 B2 | 8/2015 | Viola |
| 9,113,874 B2 | 8/2015 | Shelton, IV et al. |
| 9,161,757 B2 | 10/2015 | Bettuchi |
| 9,192,383 B2 | 11/2015 | Milliman |
| 9,192,384 B2 | 11/2015 | Bettuchi |
| 9,198,662 B2 | 12/2015 | Barton et al. |
| 9,204,878 B2 | 12/2015 | Hall et al. |
| 9,204,879 B2 | 12/2015 | Shelton, IV |
| 9,226,754 B2 | 1/2016 | D'Agostino et al. |
| 9,237,891 B2 | 1/2016 | Shelton, IV |
| 9,237,892 B2 | 1/2016 | Hodgkinson |
| 9,272,406 B2 | 3/2016 | Aronhalt et al. |
| 9,282,974 B2 | 3/2016 | Shelton, IV |
| 9,283,054 B2 | 3/2016 | Morgan et al. |
| 9,320,520 B2 | 4/2016 | Shelton, IV et al. |
| 9,326,770 B2 | 5/2016 | Shelton, IV et al. |
| 9,345,481 B2 | 5/2016 | Hall et al. |
| 9,351,731 B2 | 5/2016 | Carter et al. |
| 9,351,732 B2 | 5/2016 | Hodgkinson |
| 9,364,199 B2 | 6/2016 | Ostapoff et al. |
| 9,364,229 B2 | 6/2016 | D'Agostino et al. |
| 9,386,984 B2 | 7/2016 | Aronhalt et al. |
| 9,402,626 B2 | 8/2016 | Ortiz et al. |
| 9,402,627 B2 | 8/2016 | Stevenson et al. |
| 9,408,606 B2 | 8/2016 | Shelton, IV |
| 9,414,839 B2 | 8/2016 | Penna |
| 9,433,416 B2 * | 9/2016 | Beardsley ............... A61B 17/32 |
| 9,439,649 B2 | 9/2016 | Shelton, IV et al. |
| 9,463,018 B2 | 10/2016 | Milliman |
| 9,492,167 B2 | 11/2016 | Shelton, IV et al. |
| 9,510,828 B2 | 12/2016 | Yates et al. |
| 9,517,068 B2 | 12/2016 | Shelton, IV et al. |
| 9,526,564 B2 | 12/2016 | Rusin |
| 9,585,657 B2 | 3/2017 | Shelton, IV et al. |
| 9,585,658 B2 | 3/2017 | Shelton, IV |
| 9,592,052 B2 | 3/2017 | Shelton, IV |
| 9,592,054 B2 | 3/2017 | Schmid et al. |
| 9,597,075 B2 | 3/2017 | Shelton, IV et al. |
| 9,603,598 B2 | 3/2017 | Shelton, IV et al. |
| 9,615,826 B2 | 4/2017 | Shelton, IV et al. |
| 9,629,814 B2 | 4/2017 | Widenhouse et al. |
| 9,655,614 B2 | 5/2017 | Swensgard et al. |
| 9,681,872 B2 | 6/2017 | Jankowski et al. |
| 9,681,936 B2 | 6/2017 | Hodgkinson et al. |
| 9,687,230 B2 | 6/2017 | Leimbach et al. |
| 9,687,231 B2 | 6/2017 | Baxter, III et al. |
| 9,724,091 B2 | 8/2017 | Shelton, IV et al. |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,737,304 B2 | 8/2017 | Bettuchi et al. |
| 9,743,927 B2 | 8/2017 | Whitman |
| 9,743,928 B2 | 8/2017 | Shelton, IV et al. |
| 9,775,614 B2 | 10/2017 | Shelton, IV et al. |
| 9,848,873 B2 | 12/2017 | Shelton, IV |
| 2004/0004105 A1 | 1/2004 | Jankowski |
| 2005/0189397 A1 | 9/2005 | Jankowski |
| 2006/0085030 A1 | 4/2006 | Bettuchi et al. |
| 2006/0085032 A1 | 4/2006 | Viola |
| 2006/0085034 A1 | 4/2006 | Bettuchi |
| 2006/0108393 A1 | 5/2006 | Heinrich et al. |
| 2006/0291981 A1 | 12/2006 | Viola et al. |
| 2007/0268751 A1 | 11/2007 | Byeon et al. |
| 2008/0041918 A1 | 2/2008 | Holsten et al. |
| 2008/0140115 A1 | 6/2008 | Stopek |
| 2008/0249564 A1 | 10/2008 | Hadba et al. |
| 2008/0272175 A1 | 11/2008 | Holsten et al. |
| 2009/0001122 A1 | 1/2009 | Prommersberger et al. |
| 2009/0090764 A1 | 4/2009 | Viola |
| 2009/0152324 A1 | 6/2009 | Holsten et al. |
| 2009/0242611 A1 | 10/2009 | Hathaway et al. |
| 2009/0255974 A1 | 10/2009 | Viola |
| 2009/0277948 A1 | 11/2009 | Beardsley et al. |
| 2010/0012703 A1 | 1/2010 | Calabrese et al. |
| 2010/0016888 A1 | 1/2010 | Calabrese et al. |
| 2010/0076489 A1 | 3/2010 | Stopek et al. |
| 2010/0087840 A1 | 4/2010 | Ebersole et al. |
| 2010/0094315 A1 | 4/2010 | Beardsley et al. |
| 2010/0147921 A1 | 6/2010 | Olson |
| 2010/0147922 A1 | 6/2010 | Olson |
| 2010/0200640 A1 | 8/2010 | Viola |
| 2010/0230466 A1 | 9/2010 | Criscuolo et al. |
| 2010/0298870 A1 | 11/2010 | Hadba et al. |
| 2011/0046650 A1 | 2/2011 | Bettuchi |
| 2011/0084112 A1 | 4/2011 | Kostrzewski |
| 2011/0101070 A1 | 5/2011 | Bettuchi et al. |
| 2012/0145767 A1 | 6/2012 | Shah et al. |
| 2012/0211544 A1 | 8/2012 | Olson |
| 2012/0273548 A1 | 11/2012 | Ma et al. |
| 2012/0305628 A1 | 12/2012 | Sniffin et al. |
| 2013/0020372 A1 | 1/2013 | Jankowski et al. |
| 2013/0026209 A1 | 1/2013 | Mozdzierz et al. |
| 2013/0068818 A1 | 3/2013 | Kasvikis |
| 2013/0105548 A1 | 5/2013 | Hodgkinson et al. |
| 2013/0105549 A1 | 5/2013 | Holsten et al. |
| 2013/0112729 A1 | 5/2013 | Beardsley et al. |
| 2013/0153633 A1 | 6/2013 | Casasanta, Jr. et al. |
| 2013/0153637 A1 | 6/2013 | Hathaway et al. |
| 2013/0240600 A1 | 9/2013 | Bettuchi |
| 2013/0253535 A1 | 9/2013 | Pribanic et al. |
| 2013/0306701 A1 | 11/2013 | Olson |
| 2014/0042206 A1 | 2/2014 | Milliman |
| 2014/0048580 A1 | 2/2014 | Merchant et al. |
| 2014/0097224 A1 | 4/2014 | Prior |
| 2014/0158741 A1 * | 6/2014 | Woodard, Jr. ..... A61B 17/0401 227/175.1 |
| 2014/0158742 A1 | 6/2014 | Stopek (nee Prommersberger) et al. |
| 2014/0231488 A1 | 8/2014 | Holsten et al. |
| 2014/0239046 A1 | 8/2014 | Milliman |
| 2014/0252062 A1 | 9/2014 | Mozdzierz |
| 2014/0252070 A1 | 9/2014 | Kasvikis |
| 2014/0336641 A1 | 11/2014 | Heinrich et al. |
| 2015/0115015 A1 | 4/2015 | Prescott et al. |
| 2016/0022268 A1 | 1/2016 | Prior |
| 2016/0045200 A1 | 2/2016 | Milliman |
| 2016/0106406 A1 * | 4/2016 | Cabrera ............. A61B 17/1155 606/1 |
| 2016/0270793 A1 | 9/2016 | Carter et al. |
| 2016/0296234 A1 * | 10/2016 | Richard ............. A61B 17/1155 |
| 2016/0310143 A1 | 10/2016 | Bettuchi |
| 2016/0361057 A1 * | 12/2016 | Williams ............. A61B 17/105 |
| 2016/0374667 A1 * | 12/2016 | Miller .................. A61B 17/068 227/175.2 |
| 2016/0374677 A1 | 12/2016 | Milliman |
| 2017/0027610 A1 * | 2/2017 | Cabrera ............. A61B 17/3496 |
| 2017/0086879 A1 * | 3/2017 | Williams ........... A61B 17/1155 |
| 2017/0172575 A1 | 6/2017 | Hodgkinson |
| 2017/0196566 A1 * | 7/2017 | Sgroi ................ A61B 17/1155 |
| 2017/0224345 A1 * | 8/2017 | Cabrera ............. A61B 17/3476 |
| 2017/0231629 A1 | 8/2017 | Stopek et al. |
| 2017/0340348 A1 * | 11/2017 | Cabrera ............. A61B 17/1155 |
| 2019/0090873 A1 * | 3/2019 | Fox .................... A61B 17/1155 |
| 2020/0222050 A1 * | 7/2020 | Eisinger ............. A61B 17/1155 |
| 2020/0405304 A1 * | 12/2020 | Mozdzierz ........... A61B 17/072 |
| 2021/0000472 A1 * | 1/2021 | Sgroi, Jr. ........... A61B 17/1155 |

(56) References Cited

U.S. PATENT DOCUMENTS

| | | | |
|---|---|---|---|
| 2021/0000473 A1* | 1/2021 | Sgroi, Jr. | A61B 17/068 |
| 2021/0000500 A1* | 1/2021 | Sgroi, Jr. | A61B 17/3476 |
| 2021/0298756 A1* | 9/2021 | Eisinger | A61B 17/1155 |

FOREIGN PATENT DOCUMENTS

| | | |
|---|---|---|
| CA | 2437777 A1 | 3/1994 |
| CA | 2707255 A1 | 1/2011 |
| CA | 2829651 A1 | 5/2014 |
| CA | 2588825 C | 12/2014 |
| CN | 2778205 Y | 5/2006 |
| CN | 101332110 A | 12/2008 |
| CN | 100525720 C | 8/2009 |
| CN | 1915180 B | 7/2010 |
| CN | 101073509 B | 12/2010 |
| CN | 102038531 A | 5/2011 |
| CN | 103153159 A | 6/2013 |
| CN | 103876801 A | 6/2014 |
| CN | 105011893 A | 11/2015 |
| DE | 1835500 U | 7/1961 |
| DE | 3301713 A1 | 7/1984 |
| EP | 0152382 A2 | 8/1985 |
| EP | 0173451 A1 | 3/1986 |
| EP | 0503689 A2 | 9/1992 |
| EP | 2110084 A2 | 10/2009 |
| EP | 2116195 A1 | 11/2009 |
| EP | 2305135 A1 | 4/2011 |
| EP | 2319422 A1 | 5/2011 |
| EP | 2322103 A2 | 5/2011 |
| EP | 2401971 A2 | 1/2012 |
| EP | 2462880 B1 | 6/2012 |
| EP | 2586380 A1 | 5/2013 |
| EP | 2599451 A1 | 6/2013 |
| EP | 2649949 A1 | 10/2013 |
| EP | 2110082 B1 | 8/2014 |
| EP | 2008595 B1 | 4/2016 |
| EP | 2198787 B1 | 3/2017 |
| EP | 3135212 A1 | 3/2017 |
| EP | 3412225 A1 | 12/2018 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 119846 A1 | 11/1958 |
| WO | 8706448 A1 | 11/1987 |
| WO | 8900406 A1 | 1/1989 |
| WO | 9006085 A1 | 6/1990 |
| WO | 03053255 A1 | 7/2003 |
| WO | 03088845 A2 | 10/2003 |
| WO | 2004058080 A2 | 7/2004 |
| WO | 2006099219 A2 | 9/2006 |
| WO | 2008109123 A2 | 9/2008 |

OTHER PUBLICATIONS

Partial European Search Report dated Nov. 24, 2020, issued in corresponding EP Appln. No. 20183900, 13 pages.

* cited by examiner

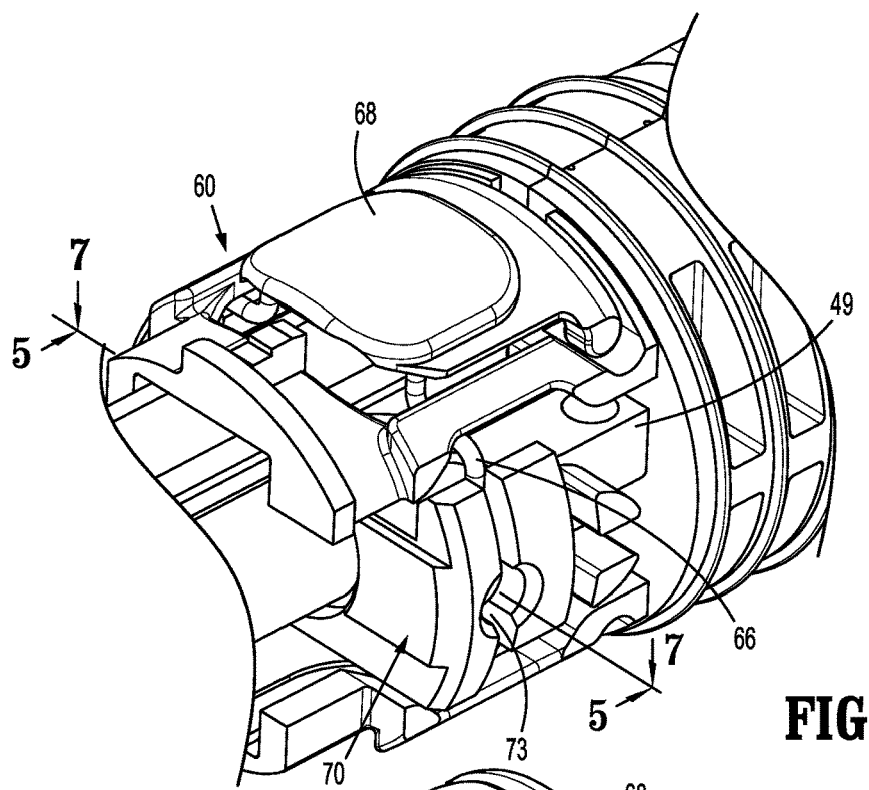
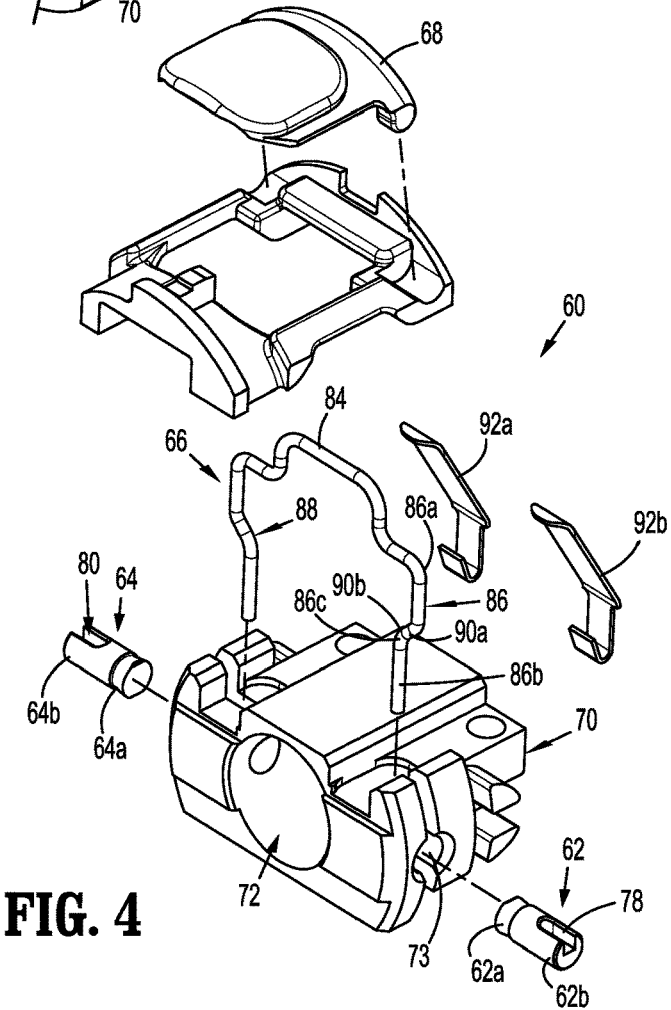
FIG. 3
FIG. 4

CIRCULAR STAPLING INSTRUMENTS

BACKGROUND

1. Technical Field

The disclosure relates to surgical devices. More specifically, the disclosure relates to handheld electromechanical circular stapling instruments for performing end-to-end anastomosis procedures.

2. Background of Related Art

Circular clamping, cutting and stapling devices may be employed in a surgical procedure to reattach colon portions that were previously transected, or to conduct similar procedures. Conventional circular clamping, cutting, and stapling devices include a pistol or linear grip-styled structure having an elongated shaft extending therefrom and a loading unit portion. The loading unit portion includes an end effector having a staple cartridge housing a plurality of staples supported on the distal end of the elongated shaft and an anvil assembly supported adjacent to the staple cartridge. During the surgical procedure, a physician may insert the loading unit portion of the circular stapling device into a rectum of a patient and maneuver the device up the colonic tract of the patient toward the transected colon portions. The anvil assembly can be purse stringed along one of the transected colon portions. Alternatively, if desired, the anvil assembly can be inserted into the colon through an incision proximal to the transected colon portion. Once properly positioned within the transected colon portions, the anvil assembly and staple cartridge are approximated toward one another and the staples are ejected from the staple cartridge toward the anvil assembly thereby forming the staples in tissue to affect an end-to-end anastomosis of the transected colon portions. An annular knife is fired to core the anastomosed colon portions. After the end-to-end anastomosis has been affected, the circular stapling device is removed from the surgical site.

The circular clamping, cutting, and stapling devices may include a powered drive system including a powered handle assembly, which may be reusable, and a disposable end effector that is removably connected to the powered handle assembly.

Many of existing end effectors for use with existing powered surgical devices and/or handle assemblies are driven by a linear driving force. For example, end effectors for performing endo-gastrointestinal anastomosis procedures, end-to-end anastomosis procedures and transverse anastomosis procedures, are actuated by a linear driving force. As such, these end effectors are not compatible with surgical devices and/or handle assemblies that use a rotary driving force.

In order to make the linear driven end effectors compatible with powered surgical devices that use a rotary driving force, adapters are used to interconnect the linear driven end effectors with the powered rotary driven surgical devices. These adapters may also be reusable, and as such, are configured to withstand multiple sterilization cycles. Prior to undergoing a sterilization process, certain components of the adapter may be removed to allow access of sterilization fluids into areas of the adapter and/or to prevent damage to vulnerable components of the adapter.

SUMMARY

According to one embodiment of the disclosure, an adapter assembly of a circular stapler is provided. The adapter assembly includes a tubular housing, a trocar assembly selectively receivable in the tubular housing, a first retention pin supported in the tubular housing, and a camming member associated with the first retention pin. The trocar assembly includes a trocar housing defining a first opening, and a trocar member axially movable within the trocar housing and configured to support an anvil assembly. The camming member is configured to move the first retention pin relative to the trocar housing between a first position and a second position. In the first position, the first retention pin is received within the first opening in the trocar housing to lock the trocar assembly with the tubular housing. In the second position, the first retention pin is removed from the first opening in the trocar housing to release the trocar assembly from the tubular housing.

In aspects, the first retention pin may define a hole and the camming member may include a first arm disposed within the hole of the first retention pin, such that movement of the first arm of the camming member moves the first retention pin between the first and second positions.

In aspects, the first arm of the camming member may have an oblique section disposed within the hole of the first retention pin.

In aspects, the first retention pin may have a first camming surface and the oblique section of the camming member may have a first camming surface configured to engage the first camming surface of the first retention pin upon a downward movement of the camming member to urge the first retention pin toward the second position.

In aspects, the first retention pin may have a second camming surface and the oblique section of the camming member may have a second camming surface configured to engage the second camming surface of the first retention pin upon upward movement of the camming member to urge the first retention pin toward the first position.

In aspects, the first arm of the camming member may have first and second longitudinal sections disposed in parallel relation to one another. The oblique section may interconnect the first and second longitudinal sections and extend inwardly in a direction from the first longitudinal section toward the second longitudinal section.

In aspects, the hole of the first retention pin may have a stepped configuration.

In aspects, the adapter assembly may further include a button movably coupled to the tubular housing. The camming member may have a backspan disposed underneath the button, such that a downward movement of the button actuates the camming member to move the first retention member from the first position toward the second position.

In aspects, the adapter assembly may further include a biasing member engaged with the backspan of the camming member and configured to resiliently bias the button toward the first position.

In aspects, the adapter assembly may further include a second retention pin supported in the tubular housing. The trocar housing may define a second opening, opposite the first opening in the trocar housing. The camming member may have a first arm associated with the first retention pin and a second arm associated with the second retention pin, such that an actuation of the camming member moves the first and second retention pins into the respective first and second openings in the trocar housing.

In accordance with another aspect of the disclosure, a surgical system may include an adapter assembly and a tip protector. The adapter assembly includes a tubular housing having a distal end portion, and a trocar assembly selectively receivable in the tubular housing. The trocar assembly includes a trocar member. The tip protector includes a housing and first and second locking members coupled to the housing. The housing defines a channel therethrough configured for receipt of the trocar member. The first locking member is configured to selectively engage the trocar member to lock the tip protector to the trocar member, and the second locking member is configured to selectively engage the distal end portion of the tubular housing to lock the tip protector to the tubular housing.

In aspects, the channel may be a counter bore including a wide channel configured for receipt of the distal end portion of the tubular housing, and a narrow channel configured for receipt of the trocar member. The first locking member may extend into the narrow channel and the second locking member may extend into the wide channel.

In aspects, the trocar member may define an aperture configured for receipt of the first locking member, and the distal end portion of the tubular housing may define an aperture configured for receipt of the second locking member.

In aspects, the tip protector may include a release button movably coupled to the housing. The release button may include a first leg associated with the first locking member, and a second leg associated with the second locking member. The first and second legs may be configured to move the respective first and second locking members out of the respective apertures in response to an actuation of the release button.

In aspects, the adapter assembly may include a first retention pin supported in the tubular housing. The first retention pin may be configured to move relative to the trocar housing between a locked state with the trocar assembly and an unlocked state with the trocar assembly. The tip protector may be configured to ensure that the first retention pin is in the locked state with the trocar assembly.

In accordance with yet another aspect of the disclosure, a tip protector for use with a circular stapler is provided. The tip protector includes a housing, first and second locking members movably coupled to the housing, and a release button movably coupled to the housing. The housing defines a channel therethrough configured for receipt of a trocar member of an adapter assembly. The first locking member is configured to selectively engage the trocar member to lock the tip protector to the trocar member. The second locking member is configured to selectively engage a tubular housing of an adapter assembly to lock the tip protector to the tubular housing. The release button is associated with each of the first and second locking members, such that an actuation of the release button moves the first and second locking members outwardly relative to the housing.

In aspects, the channel may be a counter bore including a wide channel configured for receipt of the tubular housing, and a narrow channel configured for receipt of the trocar member. The first locking member may extend into the narrow channel and the second locking member may extend into the wide channel.

In aspects, the release button may include a first leg coupled to the first locking member, and a second leg coupled to the second locking member. The first and second legs may be configured to simultaneously move the respective first and second locking members outwardly relative to the housing in response to an actuation of the release button.

In aspects, the tip protector may further include a first elongated spring element and a second elongated spring element. The first elongated spring element may have a first end portion fixed to a first side of the housing, and a free, second end portion having the first locking member coupled thereto. The second elongated spring element may have a first end portion fixed to a second side of the housing, and a free, second end portion having the second locking member coupled thereto. The first and second elongated spring elements may be configured to bias the respective first and second locking members from a non-locking position toward a locking position.

In aspects, the second elongated spring element may define a camming surface, and the second leg may define a camming surface engaged with the camming surface of the second elongated spring element, such that the second leg moves the second locking member toward the non-locking position in response to an actuation of the release button.

BRIEF DESCRIPTION OF THE DRAWINGS

Embodiments of the disclosure are described herein with reference to the accompanying drawings, wherein:

FIG. 3 is an enlarged perspective view illustrating a trocar locking assembly of the adapter assembly shown in FIG. 1 with a tubular housing of the adapter assembly removed;

FIG. 4 is a perspective view, with parts separated, of the trocar locking assembly of FIG. 3 including a button, a camming member, retention pins, a support block, and biasing members;

DETAILED DESCRIPTION

Figure 1:
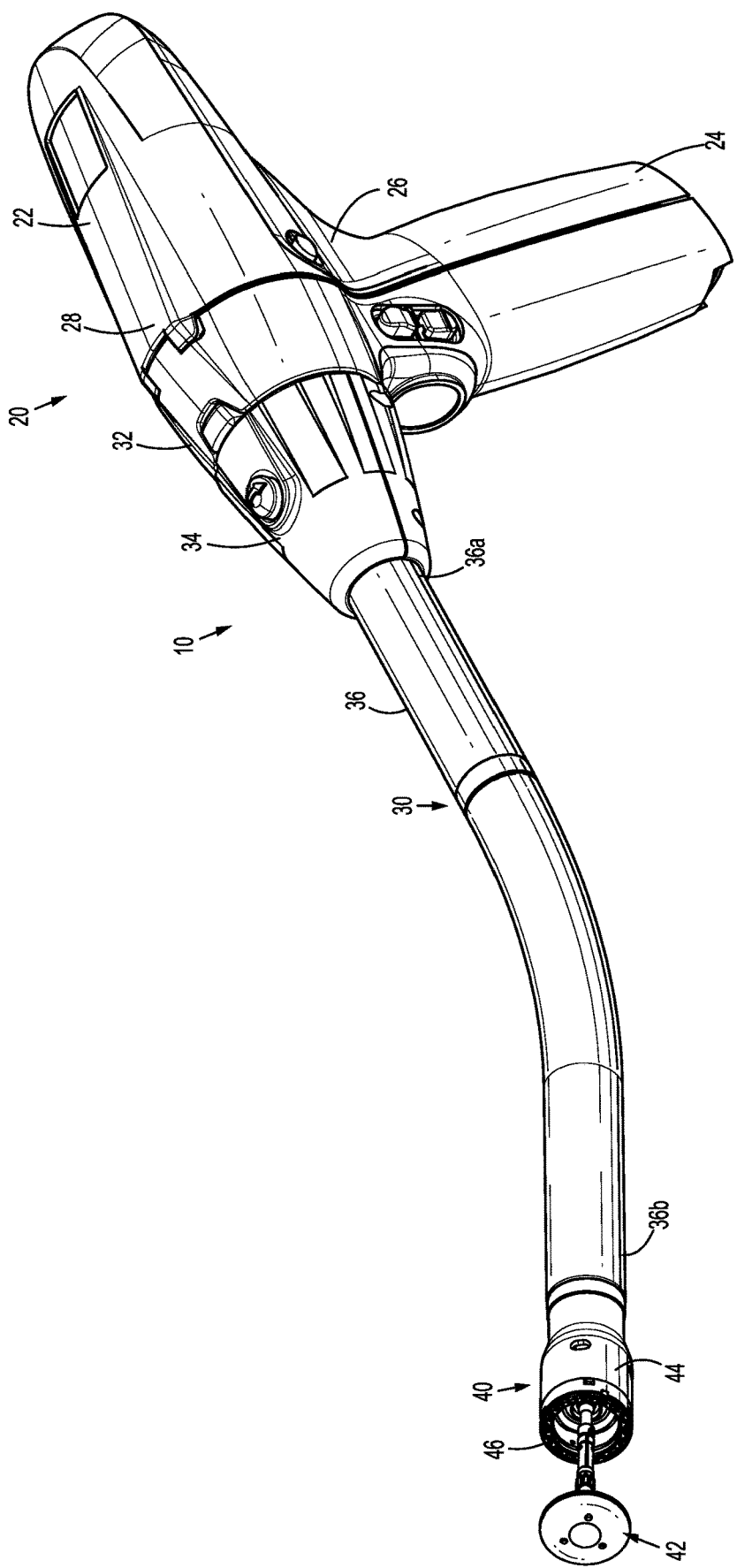
FIG. 1 is a perspective view illustrating a handheld surgical stapling instrument including a powered handle assembly, an adapter assembly, and an end effector having a reload and an anvil assembly according to an exemplary embodiment of the disclosure.

Embodiments of the disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the disclosure in unnecessary detail.

The disclosure relates to powered surgical devices having a removable trocar assembly. The trocar assembly selectively engages an anvil assembly for advancing and retracting the anvil assembly during firing of the surgical device. Components of the trocar assembly may be selectively detached from the surgical device to allow for sterilization fluids to enter the interior of the surgical device. An improved mechanism is provided for attaching the trocar assembly and maintaining attachment of the trocar assembly to an adapter assembly of the surgical device until disassembly of the trocar assembly is required.

Figure 2:
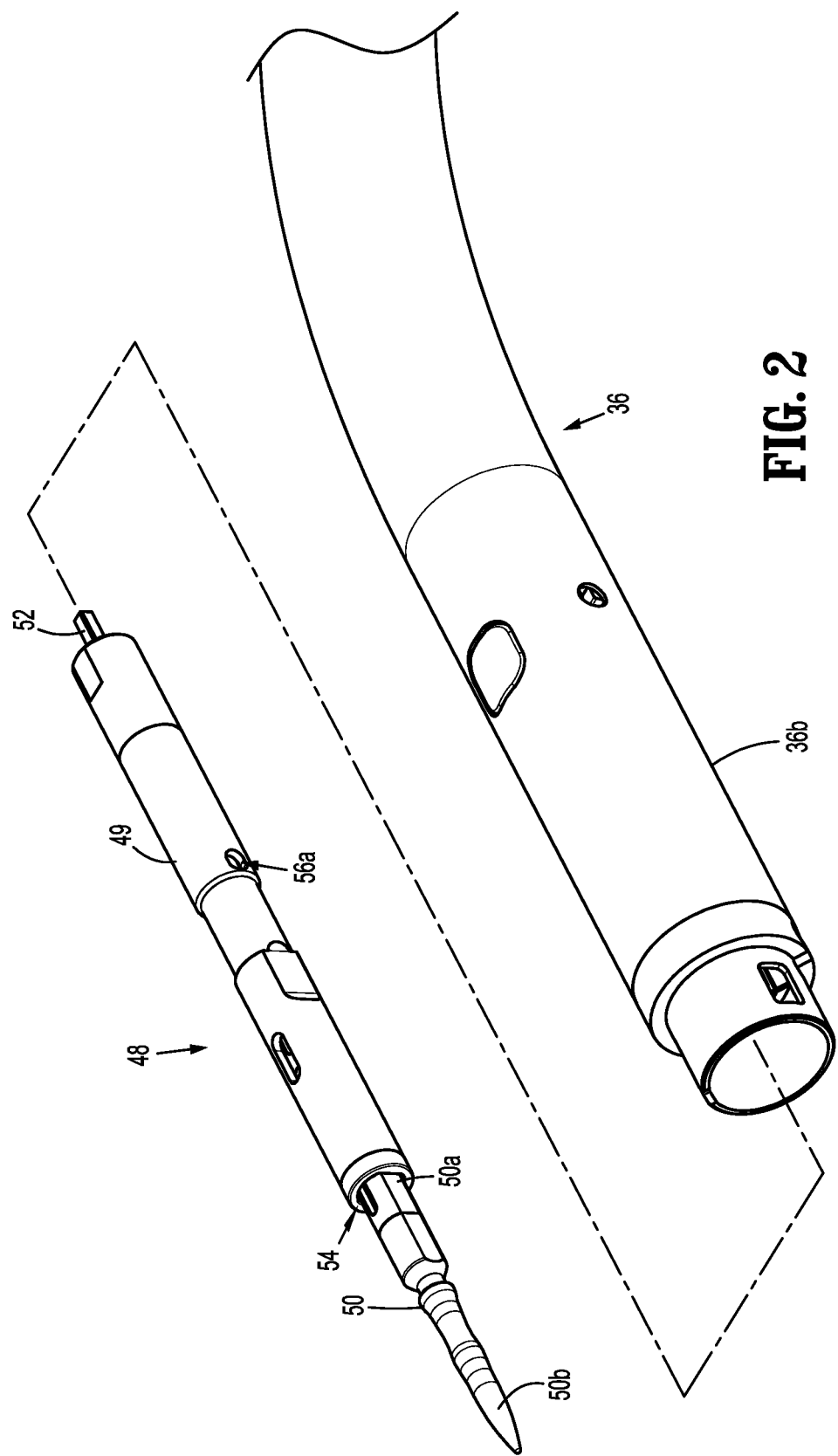
FIG. 2 is a perspective view, with parts separated, of a trocar assembly and a tubular housing of the adapter assembly of FIG. 1.

With reference to FIGS. 1 and 2, a powered surgical device 10, such as, for example, a circular stapler, includes a powered handle assembly 20, which is configured for selective connection with an adapter assembly 30, which in turn, is configured for selective connection with an end effector, such as an annular reload 40. Although generally referred to as being a powered surgical device, it is contemplated that the surgical device 10 may be a manually actuated device and may include various configurations.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. The upper housing portion 28 has a distal portion 32 that is configured to accept a proximal housing portion 34 of the adapter assembly 30.

The adapter assembly 30 includes a tubular housing 36 that includes a proximal end portion 36a that is configured for operable connection to the handle assembly 20 and an opposite, distal end portion 36b that is configured for operable connection to the reload 40. The adapter assembly 30 is configured to convert a rotational motion provided by the handle assembly 20 into axial translation that is useful for advancing/retracting a trocar member 50 of a trocar assembly 48 that is slidably disposed within the distal end portion 36b of the tubular housing 36 of the adapter assembly 30 for firing staples of the reload 40.

As best shown in FIG. 1, the reload 40 includes a housing 44 and a staple cartridge 46 fixedly secured to a distal end portion of the housing 44. The housing 44 is configured for selective connection to the distal end portion 36b of the tubular housing 36 of the adapter assembly 30. The reload 40 is configured to fire and form an annular array of surgical staples against the anvil assembly 42, and to sever or core a ring of tissue from within tissue sections being anastomosed.

For a detailed description of an exemplary powered surgical stapler including an adapter assembly and a reload, reference may be made to commonly owned U.S. Patent Application Publication No. 2016/0310134 by Contini et al., titled "Handheld Electromechanical Surgical System," filed Apr. 12, 2016, the entire contents of which being incorporated by reference herein.

With reference to FIG. 2, the trocar assembly 48 of the adapter assembly 30 includes a trocar housing 49, a trocar lead screw 52 (FIG. 5), and the trocar member 50. The trocar housing 49 defines a bore 54 that extends centrally therethrough, and a pair of opposed openings 56a, 56b (FIG. 5) that extend through an outer surface of the trocar housing 49 and communicate with the bore 54. The trocar lead screw 52 extends through the bore 54 of the trocar housing 49 and is free to rotate within the trocar housing 49 during an actuation of the handle assembly 20.

The trocar member 50 extends distally beyond the distal end portion 36b of the tubular housing 36. The trocar member 50 includes a proximal end portion 50a coupled to the lead screw 52 of the trocar assembly 48, and a distal end portion 50b configured to releasably engage an anvil assembly 42 (FIG. 1). The lead screw 52 may be threadedly coupled to the trocar member 50, such that a rotation of the lead screw 52 results in an axial translation of the trocar member 50 in response to an actuation of the handle assembly 20. When the anvil assembly 42 is connected to the trocar member 50, axial translation of the trocar member 50 in a first direction results in an opening of the anvil assembly 42 relative to the reload 40, and axial translation of the trocar member 50 in a second, opposite direction, results in a closing of the anvil assembly 42 relative to the reload 40 to capture tissue therebetween.

With reference to FIGS. 3-7, the adapter assembly 30 includes a trocar locking assembly 60 including a pair of retention pins 62, 64, a camming member 66, and a button 68. Since the first and second retention pins 62, 64 are identical or nearly identical to each other, only the first retention pin 62 will be described in detail.

The retention pins 62, 64 are supported in a support block 70 that is axially restrained within the tubular housing 36 (FIG. 2) of the adapter assembly 30. The support block 70 defines a longitudinally-extending bore 72 and transverse bores 73 that communicate with the longitudinally-extending bore 72. The trocar assembly 48 extends through the longitudinally-extending bore 72 of the support block 70. The retention pins 62, 64 are configured to move within the transverse bores 73 in the support block 70 and into the openings 56a, 56b of the trocar housing 49 to selectively lock the trocar housing 49 to the support block 70 to lock the trocar assembly 48, within the tubular housing 36 of the adapter assembly 30.

Each of the retention pins 62, 64 has a first end portion 62a, 64a configured for receipt in the openings 56a, 56b of the trocar housing 49, and a second end portion 62b, 64b slidably supported within the transverse bores 73 of the support block 70. The first end portion 62a, 64a tapers in a direction toward the second end portion 62b, 64b. The openings 56a, 56b of the trocar housing 49 have a corresponding tapered configuration to facilitate retention of the retention pins 62, 64 to the trocar housing 49, as will be described. The first end portion 62*a*, 64*a* of each of the retention pins 62, 64 defines chamfered top and bottom edges 74, 76 to ease entry of the retention pins 62, 64 into the corresponding openings 56*a*, 56*b* in the trocar housing 49.

Figure 5:
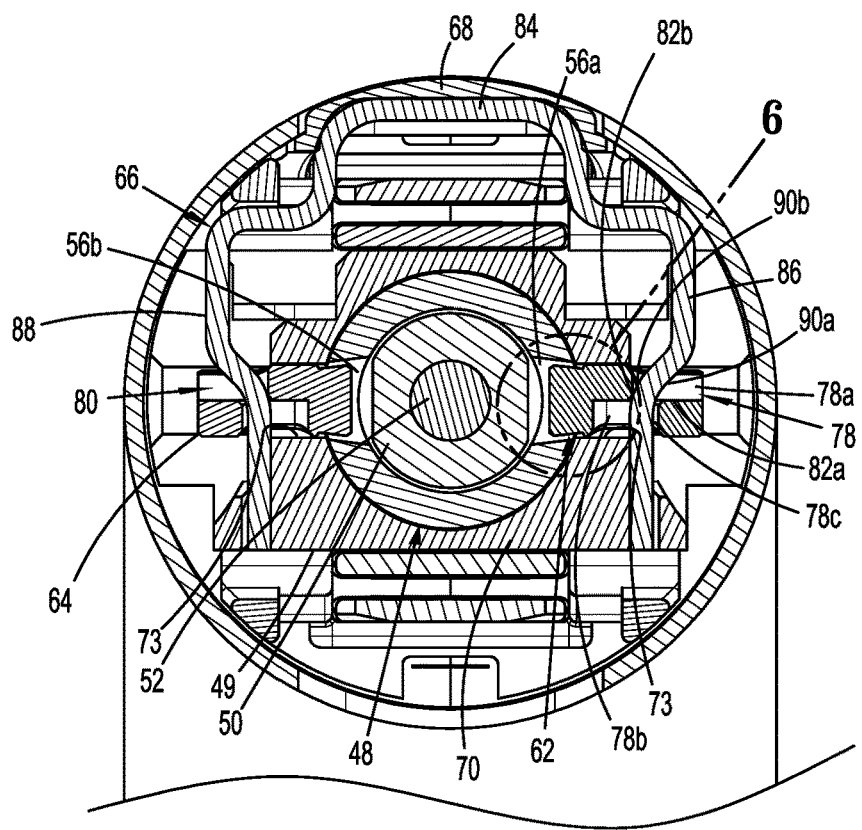
FIG. 5 is a cross-sectional view, taken alone lines 5-5 in FIG. 3, illustrating the trocar locking assembly and the trocar assembly.
Figure 6:
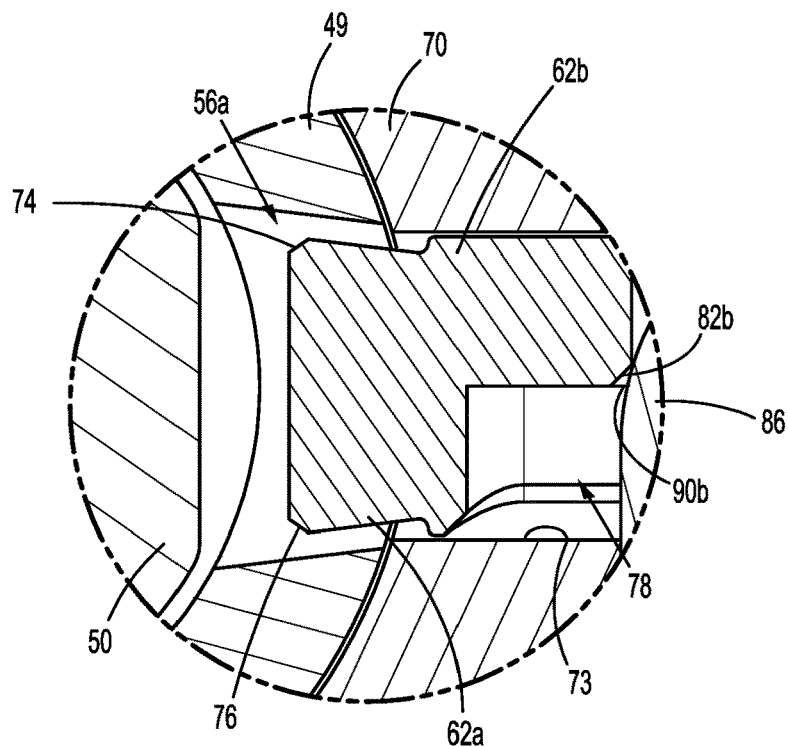
FIG. 6 is an enlarged view of the area of detail labeled 6 in FIG. 5.
Figure 7:
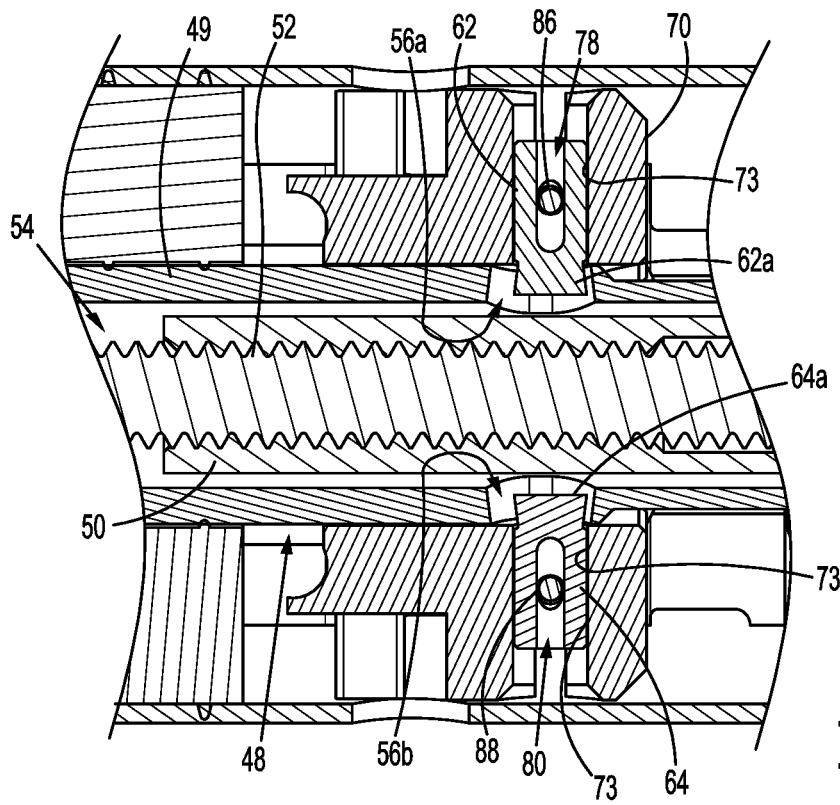
FIG. 7 is a cross-sectional view, taken along lines 7-7 in FIG. 3, illustrating retention pins of the trocar locking assembly received in openings in the trocar housing.

The second end portion 62*b*, 64*b* of each of the retention pins 62, 64 defines a stepped hole 78, respectively, through which a respective arm 86, 88 of the camming member 66 is received. In particular, and as best shown in FIG. 5, the stepped hole 78 of the retention pin 62 includes an outer segment 78*a*, an inner segment 78*b* extending parallel with the outer segment 78*a*, and an intermediate segment 78*c* connecting and extending perpendicularly between the outer and inner segments 78*a*, 78*b*. The retention pin 62 has first and second opposing camming surfaces 82*a*, 82*b* disposed within the stepped hole 78 of the retention pin 62 when the camming member 66 is coupled to the support block 70.

The camming member 66 may be fabricated from a wire and have a generally U-shaped configuration. In aspects, the camming member 66 may be fabricated from other suitable materials and assume other suitable shapes. The camming member 66 includes a backspan 84 and first and second arms 86, 88 projecting perpendicularly from respective ends of the backspan 84. The backspan 84 of the camming member 66 is disposed between the button 68 and the support block 70 or underneath the button 68 as viewed in FIG. 5. Since the first and second arms 86, 88 are identical or nearly identical, only the first arm 86 will be described in detail.

The first arm 86 of the camming member 66 has a first longitudinal section 86*a*, a second longitudinal section 86*b* that is parallel with the first longitudinal section 86*a*, and an intermediate section 86*c* interconnecting the first and second longitudinal sections 86*a*, 86*b*. The intermediate section 86*c* of the arm 86 extends at an oblique angle between the first and second longitudinal sections 86*a*, 86*b*. The intermediate section 86*c* has an outer camming surface 90*a* and an inner camming surface 90*b* that are configured to interact with the camming surfaces 82*a*, 82*b* of the retention pin 62 during actuation and de-actuation of the button 68, as will be described.

The adapter assembly 30 includes first and second biasing members 92*a*, 92*b* (FIG. 4), such as, for example, leaf springs. In aspects, the first and second biasing members 92*a*, 92*b* may be any suitable spring, such as, for example, a coil spring. The biasing members 92*a*, 92*b* are disposed between the support block 70 and the ends of the backspan 84 of the camming member 66. The biasing members 92*a*, 92*b* resiliently bias the camming member 66 and, in turn, the button 68, toward an unactuated position, in which the retention pins 62, 64 are engaged with the trocar housing 49.

Figure 9:
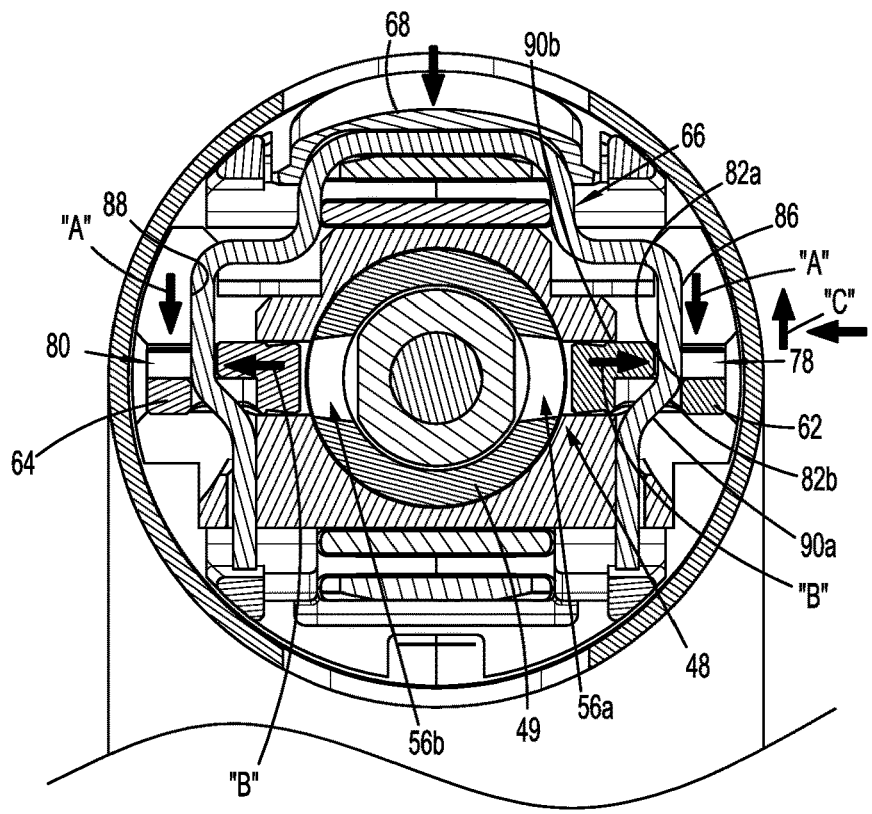
FIG. 9 is a side cross-sectional view illustrating the trocar locking assembly shown in FIG. 5 with the retention pins disengaged from the trocar assembly.

In operation, prior to or after a use of the surgical instrument 10, the surgical instrument 10 may undergo a sterilization process. To provide better access to an interior of the surgical instrument 10, the trocar assembly 48 may be disassembled from the tubular housing 36. To remove the trocar assembly 48 from the tubular housing 36 of the adapter assembly 30, the retention pins 62, 64 need to be disengaged from the openings 56*a*, 56*b* of the trocar housing 49. The button 68 may be compressed against the resilient bias of the biasing members 92*a*, 92*b*, thereby moving the arms 86, 88 of the camming member 66 through the intermediate segment 78*c* of the stepped hole 78 of each of the retention pins 62, 64. As the arms 86, 88 of the camming member 66 move through the stepped hole 78, 88, in the direction indicated by arrow "A" in FIG. 9, the outward camming surface 90*a* of the intermediate section 86*c* of the arms 86, 88 of the camming member 66 engage the inwardly-facing camming surface 82*a* of the retention pins 62, 64 to urge the retention pins 62, 64 outwardly in the direction indicated by arrow "B" in FIG. 9. With the retention pins 62, 64 disposed outside of the openings 56*a*, 56*b* in the trocar housing 49, the trocar assembly 48 is no longer locked to the tubular housing 36 and may be disengaged from the support block 70 by sliding the trocar assembly 48 from the longitudinally-extending bore 72 of the support block 70.

After sterilization and prior to use of the surgical instrument 10, the trocar assembly 48 may be loaded into the tubular housing 36 of the adapter assembly 30. To load the trocar assembly 48 into the tubular housing 36 of the adapter assembly 30, the button 68 of the trocar locking assembly 60 is compressed to move the first end portion 62*a*, 64*a* of each of the retention pins 62, 64 within the support block 70. While holding the button 68 in the compressed state, the trocar assembly 48 is loaded into the tubular housing 36 until the openings 56*a*, 56*b* in the trocar housing 49 are aligned with the transverse bores 73 of the support block 70 and the retention pins 62, 64. With the openings 56*a*, 56*b* of the trocar housing 49 aligned with the retention pins 62, 64, the button 68 is released, whereby the biasing members 92*a*, 92*b* urge both the camming member 66 and the button 68 in the direction indicated by arrow "C" in FIG. 9. As the camming member 66 moves in the direction indicated by arrow "C," the inner camming surface 90*b* of the camming member 66 engages the outwardly-facing camming surface 82*b* of the retention pins 62, 64 and urges the first end portion 62*a*, 64*a* of each of the retention pins 62, 64 into the respective openings 56*a*, 56*b* in the trocar housing 49 to lock the trocar assembly 48 with the adapter assembly 30.

Figure 10:
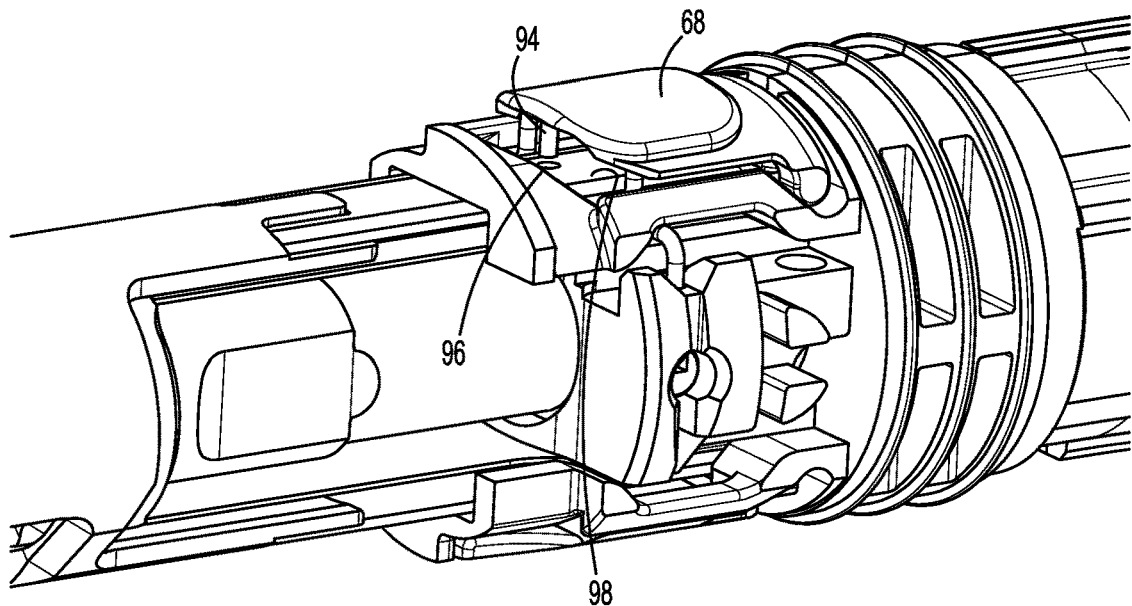
FIG. 10 is a perspective view illustrating another exemplary embodiment of the disclosed trocar locking assembly.
Figure 11:
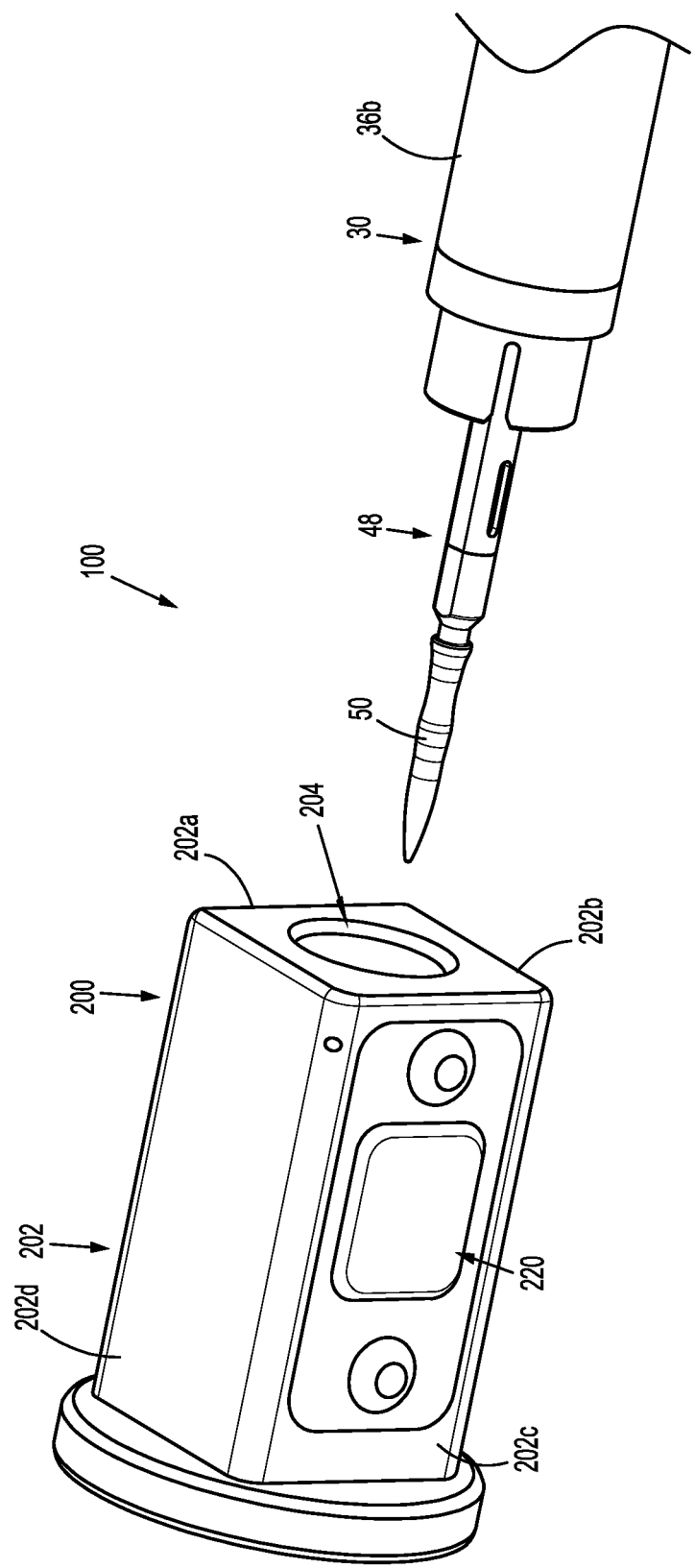
FIG. 11 is a perspective view illustrating a surgical system including the adapter assembly of FIG. 1 and a tip protector.
Figure 12:
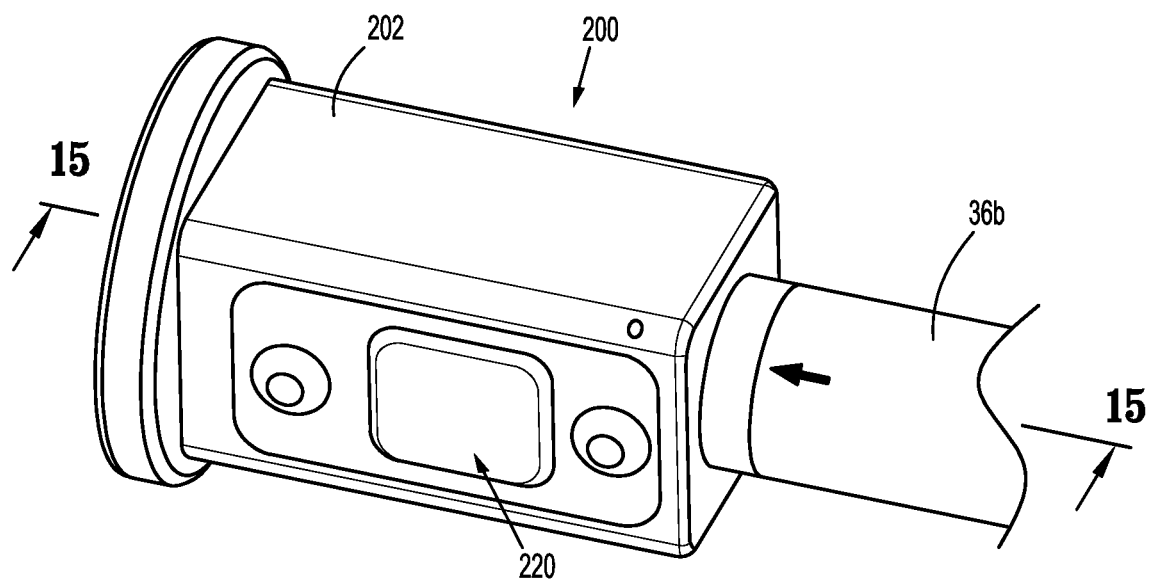
FIG. 12 is a perspective view illustrating the adapter assembly and the tip protector shown in FIG. 11 assembled to one another.

With reference to FIG. 10, the button 68 of the trocar locking assembly 60 may include a molded pin 94 extending downwardly therefrom. The molded pin 94 is configured to interact with a hole 96 of a staple band 98. When the trocar assembly 48 is to be removed, the molded pin 94 is first aligned with the hole 96 and then the button 68 may be actuated. Prior to alignment of the molded pin 94 and the hole 96, the button 68 will be prevented from being actuated. Prior to use of the surgical instrument 10, the molded pin 94 is moved out of alignment with the hole 96 to prevent inadvertent actuation of the trocar locking assembly 60. For example, once the trocar assembly 48 is inserted and locked to the tubular housing 36, the surgical instrument 10 may be calibrated to confirm the proper assembly of the trocar assembly 48. Once this is established, software stored in the handle assembly 20 (FIG. 1) triggers slight movement of the staple band 98 so that the hole 96 in the staple band 98 moves out of alignment with the pin 94. This prevents depression of the button 68, and thus prevents inadvertent un-locking of the trocar assembly 48 at any time after calibration and before the end of the procedure. Once the procedure is complete, the software can shuffle the staple band 98 back so that the trocar release button 68 can be depressed.

With reference to FIGS. 11-18, a surgical system 100 is provided including the adapter assembly 30 and a tip protector 200 for better ensuring that the trocar assembly 48 is lockingly engaged with the adapter assembly 30 prior to use. The tip protector 200 may also function as a cover the trocar assembly 48 when not in use. The tip protector 200 includes a housing 202 having a generally rectangular shape and a plurality of sides 202*a*, 202*b*, 202*c*, 202*d*. In aspects, the housing 202 may assume any suitable shape, such as cylindrical. The housing 202 defines a counter bore 204 in a proximal end thereof. The counter bore 204 includes a wide channel 204a (FIG. 14) configured for receipt of the distal end portion 36b of the tubular housing 36, and a narrow channel 204b that extends distally from the wide channel 204a and is configured for receipt of the trocar member 50 of the trocar assembly 48.

Figure 13:
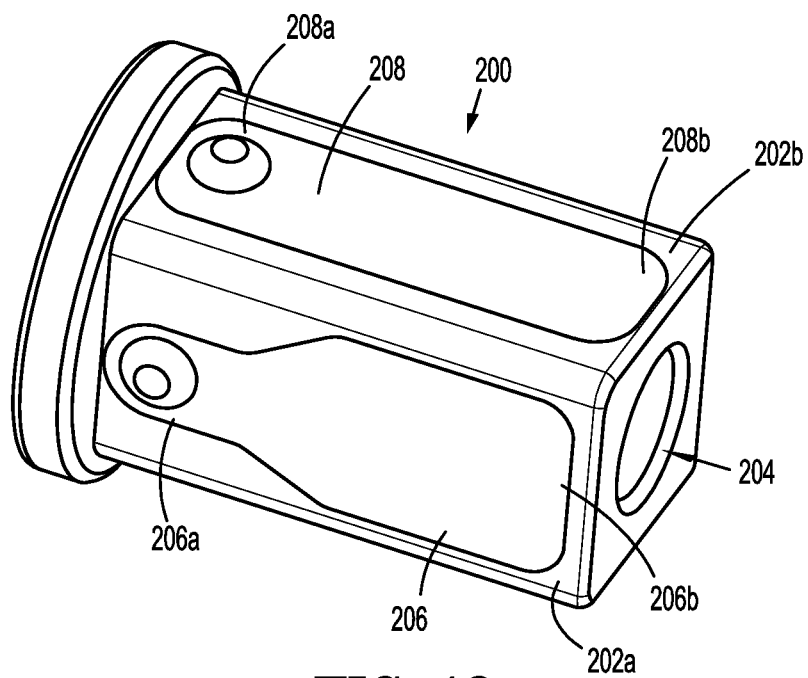
FIG. 13 is a perspective view of the tip protector of FIG. 11.
Figure 15:
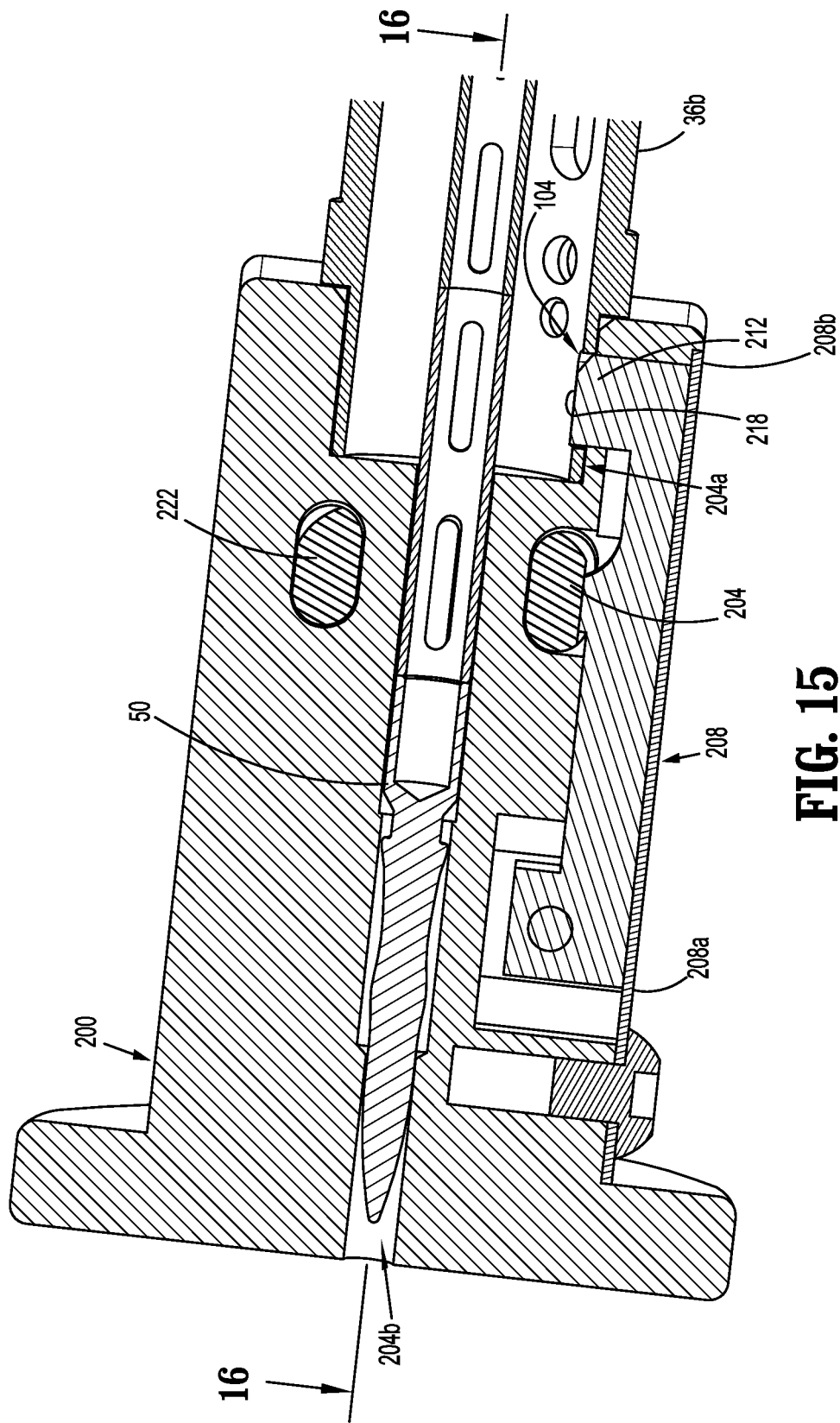
FIG. 15 is a cross-sectional view, taken along lines 15-15 in FIG. 12, illustrating the trocar assembly and the tubular housing fixed within the tip protector.
Figure 16:
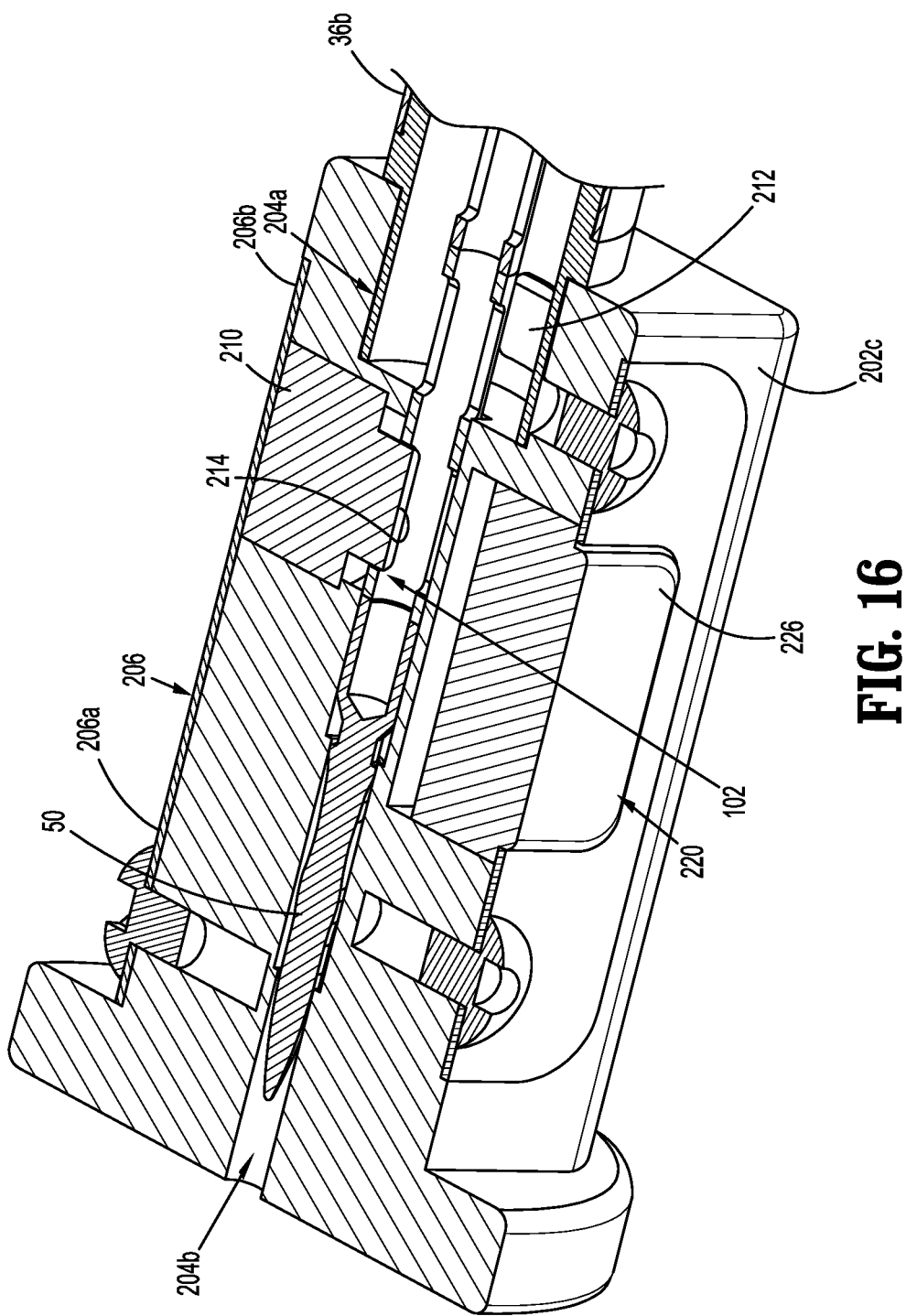
FIG. 16 is a cross-sectional view, taken along lines 16-16 in FIG. 15, illustrating first and second locking members of the tip protector engaged with the trocar member and the tubular housing, respectively.

With reference to FIGS. 13, 15, and 16, the tip protector 200 includes first and second biasing members 206, 208, such as, for example, first and second elongated spring elements coupled to adjacent first and second sides 202a, 202b of the housing 202. In aspects, the biasing members 206, 208 may be plate-like leaf springs that are supported in cantilevered fashion to the housing 202 of the tip protector 200. The first biasing member 206 has a first end 206a fixed to the housing 202, and a second end 206b free to flex relative to the first end 206a. The second biasing member 208 has a first end 208a fixed to the housing 202, and a second end 208b free to flex relative to the first end 208a.

Figure 14:
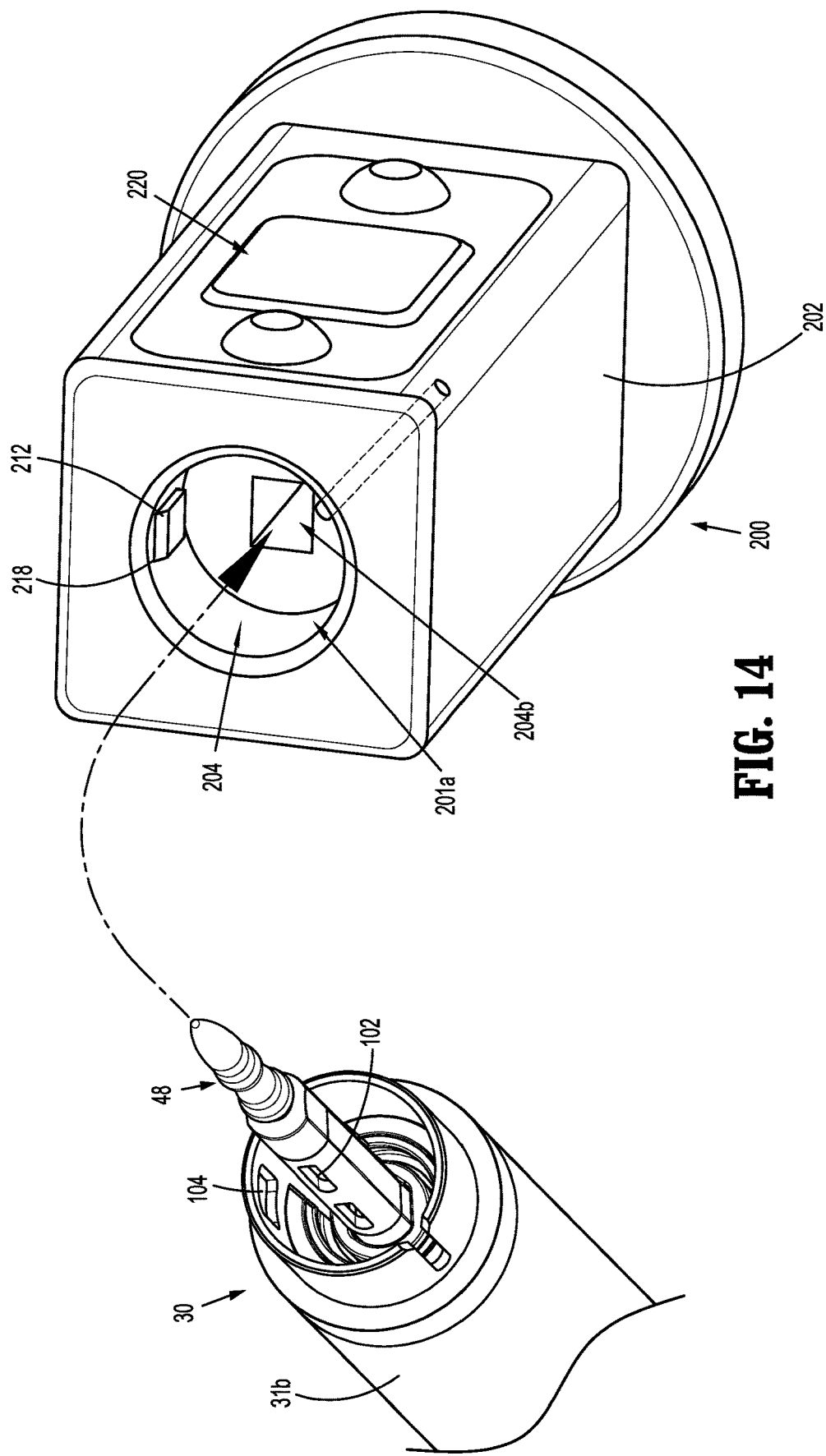
FIG. 14 is a front, perspective view illustrating the adapter assembly shown in FIG. 1 being loaded into the tip protector.

With reference to FIGS. 14-16, the tip protector 200 has first and second locking members 210, 212 movably coupled to the housing 202 of the tip protector 202. In particular, the first locking member 210 is associated with (e.g., coupled to) the second end 206b of the first biasing member 206, and the second locking member 212 is associated with (e.g., coupled to) the second end 208b of the second biasing member 208. The first locking member 210 may assume a block shape and have an engaging end 214 configured to selectively engage an aperture 102 defined in the trocar member 50. The second locking member 212 may assume a block shape and have a chamfered, engaging end 218 configured to selectively engage an aperture 104 defined in the distal end portion 36b of the tubular housing 36. In aspects, the first and second locking members 210, 212 may assume any suitable shape, such as, for example, rounded, elongated, etc. The first biasing member 206 biases the engaging end 214 of the first locking member 210 into the narrow channel 204a of the counter bore 204, and the second biasing member 208 biases the engaging end 218 of the second locking member 212 into the wide channel 204a of the counter bore 204.

Figure 17:
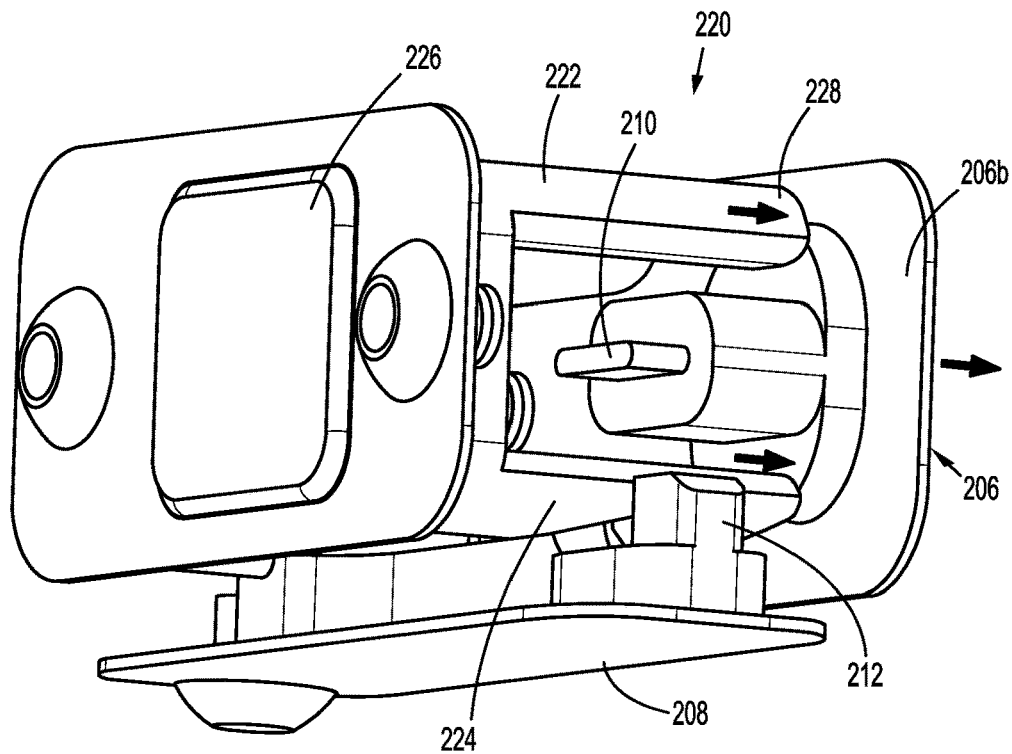
FIG. 17 is a perspective view illustrating the tip protector shown in FIG. 16, with the housing removed, and including a release button and first and second elongated spring elements.
Figure 18:
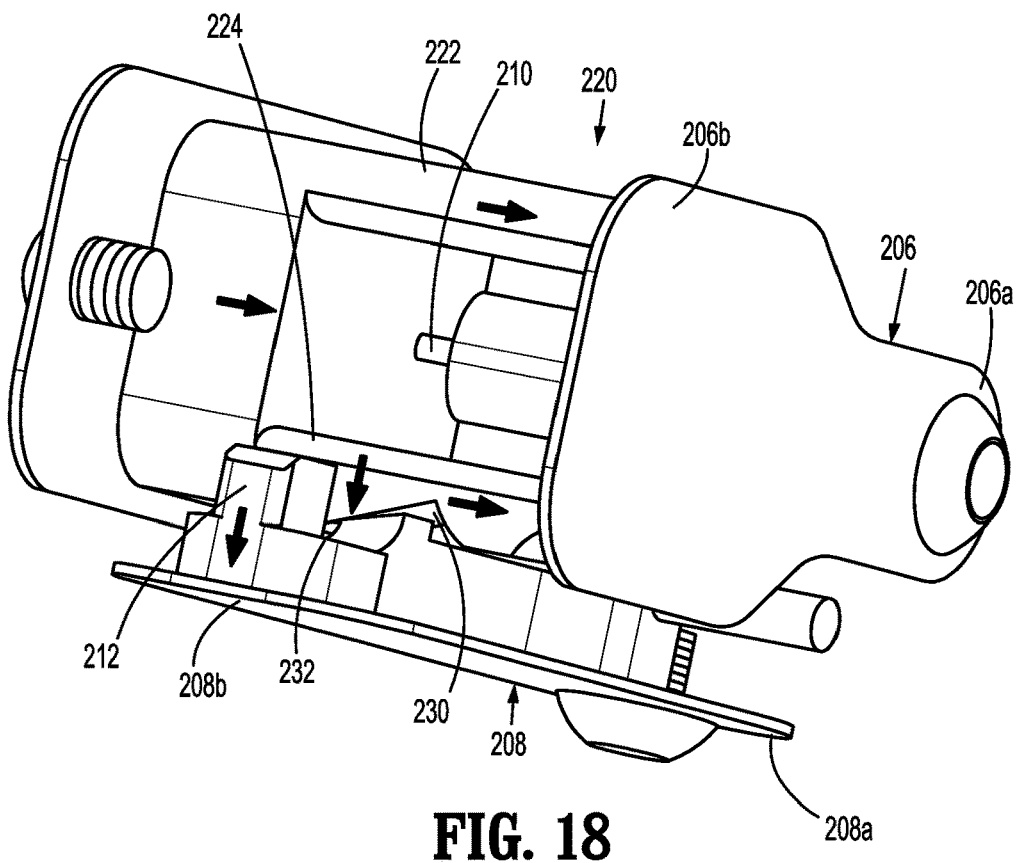
FIG. 18 is perspective view of the tip protector of FIG. 17 illustrating the release button engaged with the second elongate spring element.

With reference to FIGS. 17 and 18, the tip protector 200 includes a release button 220 movably supported in the side 202c of the housing 202 and functions to simultaneously disengage the first locking member 210 from the trocar member 50 and the second locking member 212 from the tubular housing 36b of the adapter assembly 30. The release button 220 includes a surface projection 226 extending outwardly from the side 202c of the housing 202 and first and second legs 222, 224 extending perpendicularly from the surface projection 226 into the housing 202. The surface projection 226 is configured to be acted on by a user. The first leg 222 has an end portion 228 engaged with the second end 206b of the first biasing member 206. The second leg 224 of the release button 220 has an oblique, camming surface 230 engaged with an oblique camming surface 232 attached to the second end 208b of the second biasing member 208.

In operation, to better ensure that the trocar assembly 48 is properly loaded in the tubular housing 36 of the adapter assembly 30, the tip protector 200 may be utilized. The tip protector 200 is positioned over the trocar member 50, whereby the tip of the trocar member 50 passes through the narrow channel 204b of the tip protector 200 and engages the engagement surface 214 of the first locking member 210 to urge the first locking member 210 outwardly relative to the housing 202. Movement of the tip protector 200 proximally relative to the adapter assembly 36 and/or distal movement of the adapter assembly 36 relative to the tip protector 200 is continued, whereby the distal end portion 36b of the tubular housing 36 enters the wide channel 204a of the tip protector 200 and engages the second locking member 212 of the tip protector 200. Due to the engaging end 218 of the second locking member 212 being chamfered, advancement of the tubular housing 36 into the wide channel 204a urges the second locking member 212 outwardly.

Advancement of the adapter assembly 30 through the tip protector 200 is continued until the first locking member 210 of the tip protector 200 is aligned with the aperture 102 in the trocar member 50, and the second locking member 212 of the tip protector 200 is aligned with the aperture 104 in the tubular housing 36. The first biasing member 206 biases the first locking member 210 into engagement with the aperture 102 in the trocar member 50, and the second biasing member 208 biases the second locking member 212 into engagement with the aperture 104 in the tubular housing 36. As such, the tip protector 200 is simultaneously locked (e.g., axially restrained) with the trocar member 50 of the trocar assembly 48 and the tubular housing 36 of the adapter assembly 30.

With the tip protector 200 fixed to the trocar assembly 48 and the tubular housing 36, to ensure that the trocar assembly 48 is properly engaged with the adapter assembly 30, the handle assembly 20 (FIG. 1) is actuated. Actuation of the handle assembly 20 imparts a rotational force on the trocar screw 52 of the trocar assembly 48, which exerts a distally-oriented axial force on the trocar member 50. However, since the tip protector 200 is fixed to the trocar member 50 and the tubular housing 36, rotational movement of the trocar screw 52 will not result in axial movement of the trocar member 50. In the scenario where the trocar assembly 48 is not properly engaged with the tubular housing 36, the distally-oriented axial force exerted on the trocar member 50 by the actuated trocar screw 52 drives the trocar screw 52 proximally relative to the trocar member 50 rather than advance the trocar member 50 due to the trocar member 50 being axially fixed with the tip protector 200. The trocar screw 50 retracts, along with the trocar housing 49 (FIGS. 7 and 8), until the retraction pins 62, 64 (FIGS. 7 and 8) of the trocar locking assembly 60 are aligned with and ultimately engage the corresponding openings 56a, 56b in the trocar housing 49 to lockingly engage the trocar assembly 48 with the adapter assembly 30.

Figure 8:
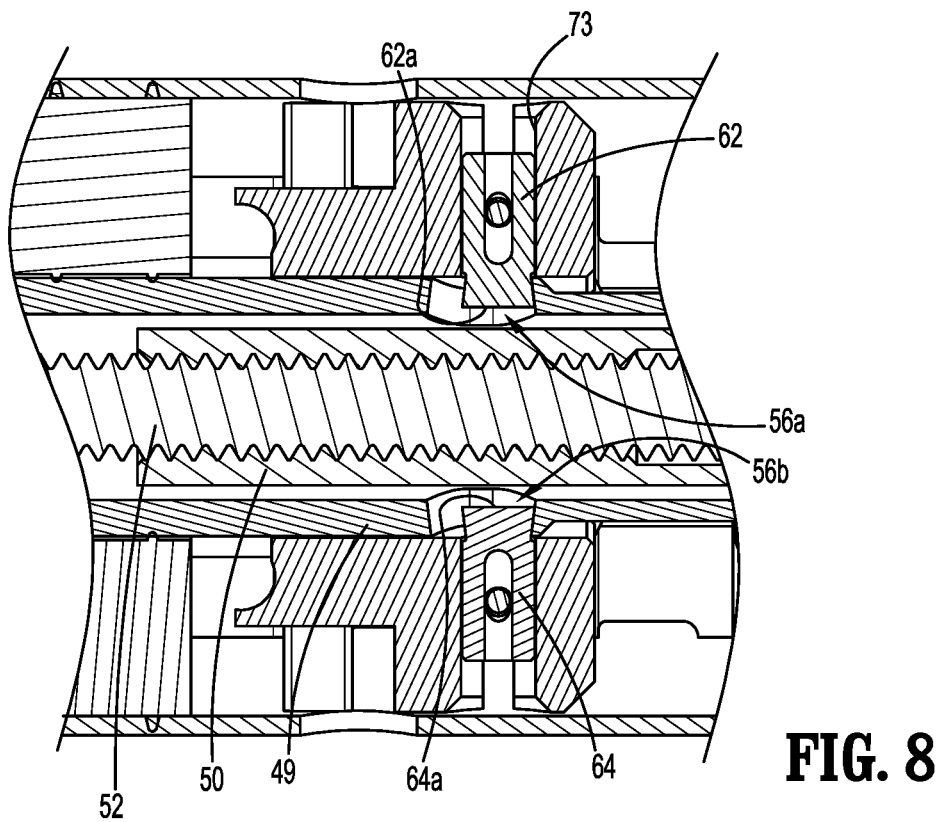
FIG. 8 is a longitudinal cross-sectional view illustrating the retention pins of the trocar locking assembly shown in FIG. 5 engaged with the trocar housing after testing the retention of the trocar assembly with the adapter assembly.

Once locked, the engagement of the trocar assembly 48 with the adapter assembly 30 may be tested by actuating the handle assembly 20. If a selected force is achieved (e.g., about 10-100 pounds), then the trocar assembly 48 is determined to be properly engaged with the adapter assembly 30. During this test, the trocar housing 49 may be moved, such that the tapered first end portion 62a, 64a of each of the retention pins 62, 64 frictionally engage the correspondingly tapered surface that defines the openings 56a, 56b of the trocar housing 49, as shown in FIG. 8. With this engagement, a greater force will be required to move the retention pins 62, 64 out of the openings 56a, 56b of the trocar housing 49. Therefore, inadvertent actuation of the button 68 (FIG. 3) of the adapter assembly 30 will not generate enough force to overcome frictional engagement between retention pins 62, 64 and the openings 56a, 56b of the trocar housing 50.

With reference to FIGS. 16-18, after it is determined that the trocar assembly 48 is properly engaged with the adapter assembly 30, the release button 220 of the tip protector 200 may be compressed. An actuation of the release button 220 moves the first leg 222 of the release button 220, which urges the second end 206b of the first biasing member 206 and the attached first locking member 210 outwardly. The first locking member 210 disengages the aperture 102 in the trocar member 50 to release the tip protector 200 from the trocar assembly 48. An actuation of the release button 220 also moves the second leg 224 of the release button 220 relative to the second biasing member 208. The movement of the second leg 224 of the release button 220 slides the camming surface 230 of the second leg 224 along the camming surface 232 of the second biasing member 208 to pivot the second end 208b of the second biasing member 208 and the attached second locking member 212 outwardly and out of engagement with the aperture 104 in the distal end portion 36b of the tubular housing 36. In this way, a single actuation of the release button 220 results in a disengagement of the tip protector 200 from both the trocar assembly 48 and the adapter assembly 30.

It will be understood that various modifications may be made to the embodiments of the disclosed adapter assemblies. Therefore, the above description should not be construed as limiting, but merely as exemplifications of embodiments. Those skilled in the art will envision other modifications within the scope and spirit of the disclosure.

What is claimed is:

1. An adapter assembly of a circular stapler, the adapter assembly comprising:
    a tubular housing;
    a trocar assembly selectively receivable in the tubular housing and including:
    a trocar housing defining a first opening having a tapered configuration; and
    a trocar member axially movable within the trocar housing and configured to support an anvil assembly;
        a first retention pin supported in the tubular housing and having a first end portion and a second end portion; and
        a camming member associated with the first retention pin, wherein the camming member is configured to move the first retention pin relative to the trocar housing between a first position, in which the first end portion of the first retention pin is received within the first opening in the trocar housing to lock the trocar assembly with the tubular housing, and a second position, in which the first end portion of the first retention pin is removed from the first opening in the trocar housing to release the trocar assembly from the tubular housing, wherein the first end portion of the first retention pin tapers in a direction toward the second end portion to strengthen the engagement of the first end portion of the first retention pin with the first opening of the trocar housing.

2. The adapter assembly according to claim 1, wherein the first retention pin defines a hole and the camming member includes a first arm disposed within the hole of the first retention pin, such that movement of the first arm of the camming member moves the first retention pin between the first and second positions.

3. The adapter assembly according to claim 2, wherein the first arm of the camming member has an oblique section disposed within the hole of the first retention pin.

4. The adapter assembly according to claim 3, wherein the first retention pin has a first camming surface and the oblique section of the camming member has a first camming surface configured to engage the first camming surface of the first retention pin upon a downward movement of the camming member to urge the first retention pin toward the second position.

5. The adapter assembly according to claim 4, wherein the first retention pin has a second camming surface and the oblique section of the camming member has a second camming surface configured to engage the second camming surface of the first retention pin upon upward movement of the camming member to urge the first retention pin toward the first position.

6. The adapter assembly according to claim 3, wherein the first arm of the camming member has a first and second longitudinal sections disposed in parallel relation to one another, the oblique section interconnecting the first and second longitudinal sections and extending inwardly in a direction from the first longitudinal section toward the second longitudinal section.

7. The adapter assembly according to claim 2, wherein the hole of the first retention pin has a stepped configuration.

8. The adapter assembly according to claim 1, further comprising a button movably coupled to the tubular housing, the camming member having a backspan disposed underneath the button, such that a downward movement of the button actuates the camming member to move the first retention member from the first position toward the second position.

9. The adapter assembly according to claim 8, further comprising a biasing member engaged with the backspan of the camming member and configured to resiliently bias the button toward the first position.

10. The adapter assembly according to claim 1, further comprising a second retention pin supported in the tubular housing, the trocar housing defining a second opening, opposite the first opening in the trocar housing, wherein the camming member has a first arm associated with the first retention pin and a second arm associated with the second retention pin, such that an actuation of the camming member moves the first and second retention pins into the respective first and second openings in the trocar housing.

11. A surgical system, comprising:
    the adapter assembly according to claim 1; and
    a tip protector including:
        a housing defining a channel therethrough configured for receipt of the trocar member;
        a first locking member movably coupled to the housing and configured to selectively engage the trocar member to lock the tip protector to the trocar member; and
        a second locking member movably coupled to the housing and configured to selectively engage a distal end portion of the tubular housing to lock the tip protector to the tubular housing.

12. The surgical system according to claim 11, wherein the channel is a counterbore including a wide channel configured for receipt of the distal end portion of the tubular housing, and a narrow channel configured for receipt of the trocar member, the first locking member extending into the narrow channel and the second locking member extending into the wide channel.

13. The surgical system according to claim 11, wherein the trocar member defines an aperture configured for receipt of the first locking member, and the distal end portion of the tubular housing defines an aperture configured for receipt of the second locking member.

14. The surgical system according to claim 13, wherein the tip protector includes a release button movably coupled to the housing and having:
    a first leg associated with the first locking member; and a second leg associated with the second locking member, the first and second legs configured to move the respective first and second locking members out of the respective apertures in response to an actuation of the release button.

15. The surgical system according to claim 11, wherein the first retention pin is configured to move relative to the trocar housing between a locked state with the trocar assembly and an unlocked state with the trocar assembly, the tip protector configured to ensure that the first retention pin is in the locked state with the trocar assembly.

16. The adapter assembly according to claim 8, further comprising a staple band disposed underneath the button and defining a hole, wherein the button includes a pin extending downwardly therefrom and configured for passage through the hole of the staple band, the staple band configured to move relative to the button between a first position, in which the pin of the button is aligned with the hole of the staple band, and a second position, in which the staple band prevents actuation of the button.

* * * * *